(12) United States Patent
Cohen

(10) Patent No.: US 8,986,613 B2
(45) Date of Patent: Mar. 24, 2015

(54) DISPOSABLE USB CUP

(75) Inventor: Zeev Cohen, Zichron-Yaakov (IL)

(73) Assignee: Flometrica Ltd., Zichron-Yaakov (IL)

( * ) Notice: Subject to any disclaimer, the term of this patent is extended or adjusted under 35 U.S.C. 154(b) by 549 days.

(21) Appl. No.: 13/384,805

(22) PCT Filed: Jul. 22, 2010

(86) PCT No.: PCT/IL2010/000585
§ 371 (c)(1),
(2), (4) Date: Jan. 19, 2012

(87) PCT Pub. No.: WO2011/010311
PCT Pub. Date: Jan. 27, 2011

(65) Prior Publication Data
US 2012/0123233 A1    May 17, 2012

Related U.S. Application Data

(60) Provisional application No. 61/228,438, filed on Jul. 24, 2009, provisional application No. 61/329,740, filed on Apr. 30, 2010.

(51) Int. Cl.
*G01N 27/327*    (2006.01)
*A61B 10/00*    (2006.01)

(52) U.S. Cl.
CPC ............ *A61B 10/007* (2013.01); *A61B 10/0096* (2013.01)
USPC .......................... 422/82.01; 204/400; 205/792

(58) Field of Classification Search
CPC . G01N 33/48; G01N 27/3273; G01N 27/403; A61B 5/207
See application file for complete search history.

(56) References Cited

U.S. PATENT DOCUMENTS

| 5,062,304 A | 11/1991 | Van Buskirk |
| 6,138,508 A | 10/2000 | Hannan et al. |

(Continued)

FOREIGN PATENT DOCUMENTS

| CN | 2890919 Y | 3/2008 | |
| EP | 0342028 A | * 11/1989 | ............ A61B 10/00 |

(Continued)

OTHER PUBLICATIONS

JPO machine-generated English language translation of the abstract and Figures 1 and 2 of Yuji Nakamurai JP 04-033643 A, patent published Feb. 5, 1992.*

(Continued)

*Primary Examiner* — Alex Noguerola
(74) *Attorney, Agent, or Firm* — Roach Brown McCarthy & Gruber, P.C.; Kevin D. McCarthy

(57) ABSTRACT

The present invention provides a handheld USB Cup for use in collection of a fluidic body sample, comprising ad receptacle comprising side surfaces, a bottom plate and a sensor assembly, the sensor assembly comprising at least one sensor and a slave circuitry; said sensor assembly is permanently affixed to said side surfaces or said bottom plate. The receptacle is capable of maintaining the fluidic body sample for a sufficient time period in the vicinity of the sensor thereby the sensor is operative to provide continuous measurement of an electric, chemical or physical property of the urine. The slave circuitry responds to the electric, chemical or physical property of the fluidic body sample received from the sensor and is configured and operable to electronically communicate the measurement of the electric, chemical or physical property of the fluidic body sample to an external processing master unit.

19 Claims, 17 Drawing Sheets

(56) References Cited

U.S. PATENT DOCUMENTS

| | | |
|---|---|---|
| 2004/0199131 A1 | 10/2004 | Kitamura |
| 2005/0288608 A1 | 12/2005 | Corcos |
| 2007/0006368 A1* | 1/2007 | Key ............................... 4/144.2 |
| 2008/0060422 A1* | 3/2008 | Hosoya ......................... 73/53.01 |
| 2008/0278337 A1* | 11/2008 | Huang et al. ................. 340/573.5 |

FOREIGN PATENT DOCUMENTS

| | | | |
|---|---|---|---|
| EP | 1 901 058 | 3/2008 | |
| JP | 04-033643 A * | 2/1992 | ............... A61B 5/20 |
| JP | 2005-030788 | 2/2005 | |
| JP | 2005-172493 A * | 6/2005 | ............. G01N 27/28 |
| JP | 2009-258078 | 11/2009 | |
| WO | 2005/057210 | 6/2005 | |
| WO | 2007/111001 | 10/2007 | |
| WO | 2008/129640 | 10/2008 | |
| WO | 2009052496 A1 | 4/2009 | |

OTHER PUBLICATIONS

JPO machine-generated English language translation of Goto et al. JP 2005-172493 A, patent published Jun. 30, 2005.*

IPRP CH I for PCT/IL2010/000585, 11 pages, mailed on Jan. 24, 2012.

* cited by examiner

Normal

| Results | |
|---|---|
| 0 Max | 27 ml/s |
| 0 Avg | 18 ml/s |
| T Flow | 23 sec |
| T Void | 23 sec |
| T to Max | 7 sec |
| Volume | 485 ml |
| PVR | —— ml |

Intermittent

| Results | |
|---|---|
| 0 Max | 7 ml/s |
| 0 Avg | 6 ml/s |
| T Flow | 21 sec |
| T Void | 37 sec |
| T to Max | 24 sec |
| Volume | 128 ml |
| PVR | —— ml |

Obstructed

| Results | |
|---|---|
| 0 Max | 5 ml/s |
| 0 Avg | 5 ml/s |
| T Flow | 57 sec |
| T Void | 57 sec |
| T to Max | 18 sec |
| Volume | 253 ml |
| PVR | —— ml |

DISPOSABLE USB CUP

REFERENCE TO CO-PENDING APPLICATIONS

Priority is claimed as a 371 of international application number PCT/IL2010/000585, filed on Jul. 22, 2010; which claims priority to U.S. Provisional Patent application numbers (a) 61/228,438, filed on Jul 24, 2009 and (b) 61/329,740, filed on Apr. 30, 2010.

FIELD OF THE INVENTION

This invention relates to devices and methods for fluid measurements and in particular, measurements of urine.

BACKGROUND OF THE INVENTION

Lower Urinary Tract Symptoms (LUTS) are a common problem affecting approximately 50% of men over the age of 40. Filling or irritative symptoms include: interruption of urination frequency, urination urgency, Dysuria and Nocturia. Voiding or obstructive symptoms include: a poor stream, hesitancy, terminal dribbling, incomplete voiding and overflow incontinence. Diagnostics of the above symptoms is achieved by referring the patients to undertake a urine flow test. Using the currently available testing method, the patient urinates into a urine flow meter test machine. The results serve as a preliminary diagnostic tool for the physicians.

WO2007/111001 provides an apparatus including: a container that receives urine; and a urine amount measuring device that measures the weight of the urine received by the container; wherein the urine amount measuring device has: a mounting plate, which is a plate on which the container is mounted; a measuring portion that measures the weight of the container mounted on the mounting plate multiple times at given time intervals; and an output portion that outputs a result of the measurement performed by the measuring portion, and the apparatus has a fixing structure that is situated in at least a bottom portion of the container and a mounting face of the mounting plate and that detachably fixes the container on the mounting plate.

The existing urine measurement devices generally posses a plurality of inherent pitfalls:

(i) Conventional testing is not done at physiological conditions;

(ii) The measurement devices are not hygienic since it is practically impossible to urinate only to the container and urine contaminates the measuring device. These devices require cleaning and skilled maintenance to operate properly.

(iii) Some devices have a removable receptacle having no sensors being in sensing vicinity with the urine or other fluidic body sample; these devices did not address the problem of contamination of other parts of the measuring device nor provide accurate urine measurements.

(iv) Weight based devices sample the weight only several times a second hence they are limited in flow sensitivity.

(v) Other devices operate on the principle of creating air pressure changes in a locked chamber due to urine administered to the chamber. These devices are very limited in accuracy and susceptible to temperature changes created by the urine, Atmospheric pressure, and the need to keep the air chamber 100% sealed for the measurement to take place accurately.

Current devices for measuring urine measurements in general are cumbersome, or employ rather inaccurate methodologies for urine measurement. The equipment used requires cleaning and maintenance and is typically operated by professional trained staff, therefore normally available only in hospitals or clinics.

SUMMARY OF THE INVENTION

The present invention introduces devices, assemblies and kits ensuring continuous, repeated and accurate urine measurements, and maintaining the reliability of the measurements while being performed remotely in the private settings of the user without clinical assistance, and further permitting the physician to obtain optimized, accurate and substantially error-free medical data.

Thus, the present invention provides a handheld integrated urine collection vessel, comprising:
 a single use disposable receptacle comprising side surfaces;
 a bottom plate; and
 a single use disposable sensor assembly, the sensor assembly comprising at least one sensor and a slave circuitry; the sensor assembly is permanently affixed to the side surfaces or the bottom plate.

In some embodiments, the receptacle is configured to facilitate accurate urine measurement insensitive to the horizontal angle of the receptacle.

During urine measurement, the receptacle maintains the urine for a sufficient time period in the vicinity of the sensor thereby the sensor is operative to provide continuous measurement of an electric or chemical property of the urine; the slave circuitry responds to electric, chemical or physical property of the urine received from the sensor and is configured and operable to electronically communicate the measurement of an electric, chemical or physical property of the urine to an external processing master unit.

In one embodiment, the present invention provides a handheld USB Cup for use in collection of a fluidic body sample, comprising: a receptacle comprising side surfaces, a bottom plate and a sensor assembly, the sensor assembly comprising at least one sensor and a slave circuitry; said sensor assembly is permanently affixed to said side surfaces or said bottom plate;
 wherein the receptacle is capable of maintaining the fluidic body sample for a sufficient time period in the vicinity of the sensor thereby the sensor is operative to provide continuous measurement of an electric, chemical or physical property of the urine; said slave circuitry responds to the electric, chemical or physical property of the fluidic body sample received from the sensor and is configured and operable to electronically communicate the measurement of the electric, chemical or physical property of the fluidic body sample to an external processing master unit; wherein the handheld USB Cup is removably attachable from the external processing master unit, defining an attached configuration and a detached configuration and thereby facilitating electronic communication between the sensor assembly and the external processing master unit.

In second aspect, the present invention provides a handheld device for recording urine measurements, the device is configured and adapted to electronically communicate with the handheld urine collection vessel disclosed herein; the device comprises the processing master unit to receive and process the measurement of an electric, chemical or physical property of the urine being obtained from the sensor or sensor plate; the device generates an output signal indicative of the urine measurement being performed which includes the results of the test or measurement.

In another aspect, a hardware dongle device for providing a 24 hour urination diary is provided. The dongle device comprises a master processing unit, a frequency dependent component, memory component, an electric interface, real-time clock, and a communication port; the device is configured and adapted to electronically communicate, receive and process an external measurement of an electric, chemical or physical property of the urine being obtained from an external urine collection vessel and processed by the frequency dependent component; the external collection vessel have a sensor assembly comprising slave circuitry being controlled by the master processing unit; said device generates an output signal indicative of the urine measurement and records the output signal and a time stamp being obtained from the real-time clock in the memory component; the device determine and accumulates a plurality of separate urine measurements and associates them with time stamps; thereby recording a 24 hour urination profile of a tested individual.

The dongle can be removably attachable from the disposable urine receptacle, defining an attached configuration and a detached configuration and thereby facilitating electronic communication between the sensor and the external processing master unit.

DESCRIPTION OF THE DRAWINGS

In order to understand the invention and to see how it may be carried out in practice, embodiments will now be described, by way of non-limiting example only, with reference to the accompanying drawings, in which:

FIG. 1A is a schematic illustration of the fluid receptacle and an insertable USB based handheld device for recording the measurements; FIG. 1B shows the fluid receptacle in an attached configuration.

FIG. 2A shows a side view of an exemplary fluid receptacle having a conductive plate configuration; FIG. 2B shows a top view of the fluid receptacle having a conductive plate configuration; FIG. 2C is an example of a passive circuitry fixed onto the receptacle.

FIG. 3A is a side isometric view of an exemplary fluid receptacle; FIG. 3B is another side isometric view of the exemplary fluid receptacle; FIG. 3C is a top isometric view of the exemplary fluid receptacle; FIG. 3D is a an isometric view; FIG. 3E is a side cross-sectional view of the exemplary fluid receptacle; and FIG. 3F is an exploded view of the exemplary fluid receptacle;

FIG. 4A shows a bottom isometric view of an exemplary fluid receptacle removably fixated on a toilet seat; FIG. 4B shows an elevated isometric view of the exemplary fluid receptacle removably fixated on a toilet seat.

FIG. 6A shows a schematic diagram of a 555 circuit which can be used for analysis of measured data. FIG. 6B shows the 555 circuit being configured and wired to the integrated urine collection vessel for receiving the measured data.

DETAILED DESCRIPTION OF EMBODIMENTS

Figure 1A:
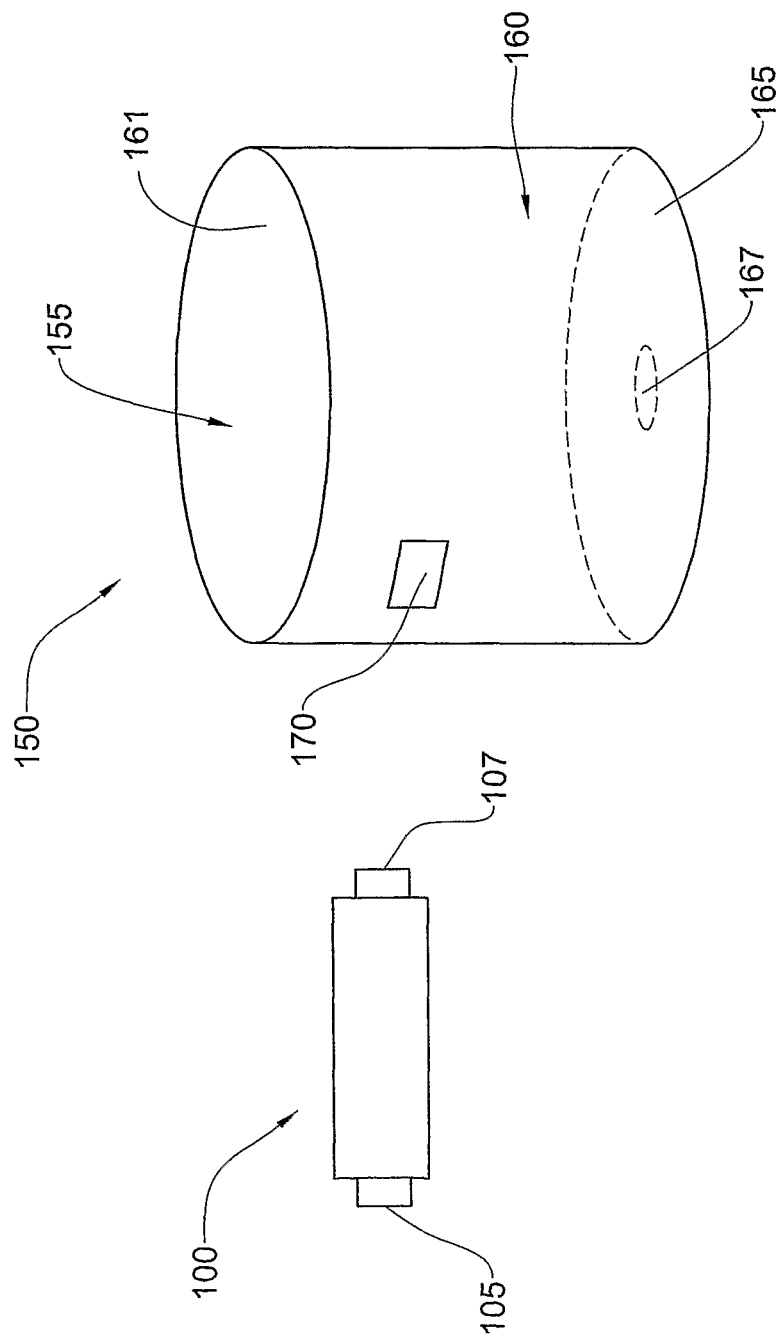
FIGS. 1A-1B.

Unlike the conventional urine measurement devices, the inventor has found that in order to facilitate urine measurements or measurement of another fluidic body sample remotely in the private settings as opposed to the clinical settings (with trained medical staff), the conventional methodologies are inappropriate. The present invention therefore provides devices, assemblies and kits ensuring continuous and accurate urine measurements while being performed remotely in the private settings of the user without clinical assistance, permitting the physician to obtain optimized medical data.

The present invention provides accurate urine measurements in the private settings at a reduced price as compared to the available urine flow meters.

Quality control and accuracy of the fluid measurements (e.g. urine flow measurement) is achieved by relieving the user from the need to appropriately prepare the measuring device to the next (or successive) measurement round. It was found that having the user prepare the measuring device introduces a subjective factor to the measurement process which reduces reliability on one hand, and also reduces the cooperative participation by the user. As disclosed herein, the physician can propose the user a handheld recording device and a kit comprising plurality of single use disposable urine receptacles each having a disposable sensor assembly including sensor(s) and a slave circuitry. In the context of the present invention, the disposable containers of the present invention are referred to as a "USB Cup". The slave circuitry responds to electric or chemical property of the urine received from the disposable sensor and is configured and operable to electronically communicate the measurement of an electric or chemical property or physical of the urine to an external processing master unit. Following the performance of a urine measurement, the disposable receptacle can be disposed of, and the handheld device is readily available (ready to use) immediately without any additional preparatory step. The handheld device thus accumulates measured data which can be sent to a remote unit for analysis.

The present invention thus discloses utilization of a disposable container (or receptacle) which comprises a disposable sensor assembly including at least one sensor to measure a body sample in the form of fluid. The disposable container is configured and operable to communicate with a handheld electronic device which acts as a master processing unit. This master unit permit accumulation of the urine sample measurements over time, while the actual sensing assembly and collection vessel (receptacle) being disposed of replaced by another alike kit member.

Unlike urine measuring devices which provide a single output measurement, the present invention thus further provides an automated urination diary. The handheld electronic device can thus be configured to operate as an automated urination diary.

In some embodiments, the "USB cup" can be a single-use disposable member while the master unit is a multiple use member configured to collect, memorize and/or analyze data retrieved in at least one, most or all uses.

The automated urination diary thus accumulates urine measurements which were electronically communicated from the disposable container. This data accumulation can be performed in an automated manner without the need to involve the user in inserting the measured data in a manual manner. The accumulated data can include a time stamp which is the time in which the measurement was performed. The accumulated data can also include the test results or the measured and processed data.

The present invention therefore further discloses a diagnostic device permitting 24 hour monitoring of urination diary. This makes urination diary accurate and less susceptible to human errors especially in cases where Nocturia or elderly or special needs population are involved.

In the present invention, "about" shall mean +/−10%.

In one embodiment, a handheld integrated urine collection vessel 150 is provided. Therefore, the handheld integrated urine collection vessel comprises a single use disposable receptacle comprising inner and exterior side surfaces 160, 161 (respectively); and a bottom plate 165. The bottom plate can at least partially forces the collected urine to accumulate at about the side surfaces 160.

The vessel further includes a single use disposable sensor assembly, the sensor assembly comprising at least one sensor and a slave circuitry which can take, at least in part, the form of wiring; the sensor assembly is permanently affixed to the side surfaces 160, or the bottom plate. In some embodiments, the receptacle is configured to facilitate accurate urine measurement insensitive to the horizontal angle of the receptacle. In some embodiments, this configuration forces or maintains uniform liquid distribution of the urine on the bottom plate 165 as also further elaborated below. This can be facilitated by the combination of structures of both the receptacle and a disposable funnel component. The sensor assembly can be permanently affixed to the exterior side surface 160 or alternatively to the inner side wall 161.

In another embodiment, the present invention provides a handheld USB Cup for use in collection of a fluidic body sample, comprising a receptacle comprising side surfaces, a bottom plate and a sensor assembly, the sensor assembly comprising at least one sensor and a slave circuitry; said sensor assembly is permanently affixed to said side surfaces or said bottom plate. The receptacle is capable of maintaining the fluidic body sample for a sufficient time period in the vicinity of the sensor thereby the sensor is operative to provide continuous measurement of an electric, chemical or physical property of the urine. The slave circuitry responds to the electric, chemical or physical property of the fluidic body sample received from the sensor and is configured and operable to electronically communicate the measurement of the electric, chemical or physical property of the fluidic body sample to an external processing master unit.

In some embodiments, the handheld USB Cup is removably attachable from the external processing master unit, defining an attached configuration and a detached configuration and thereby facilitating electronic communication between the sensor assembly and the external processing master unit.

It should be noted that in 300 the vessel is in an attached configuration with a handheld electronic device of the present invention being connected therewith. The handheld electronic device can also be referred to as an external processing master unit, both terms are used herein interchangeably. As it will be explained herein the handheld electronic device can be further configured and adapted as stationary and also alternatively as a dongle device operating as urination diary.

During urine measurement, the receptacle maintains the urine for a sufficient time period in the vicinity of the sensor thereby the sensor is operative to provide continuous measurement of an electric or chemical property of the urine; the slave circuitry responds to electric, chemical or physical property of the urine received from the sensor and is configured and operable to electronically communicate the measurement of an electric, chemical or physical property of the urine to an external processing master unit.

In some embodiments, the handheld integrated urine collection vessel 150 is configured to provide fluid contact between urine and the at least one sensor.

By way of none limiting example, yet another handheld integrated collection vessel of a bodily fluid is provided. In accordance with the present embodiment, the handheld integrated collection vessel 200 comprises a single use disposable receptacle for collection of a conductive bodily fluid comprising: inner and exterior side surfaces (205, 206 respectively); and a bottom plate 215; the side surfaces can comprise a dielectric substance; a first conductive plate 210 is permanently coupled to at least a portion the exterior side surface so as to define a capacitive sensing volume 250 within the receptacle and facing a surface area of the first conductive plate; the collection vessel is configured and operable to continuously collect and maintain the conductive bodily fluid in fluid contact with the inner side surface 206 during a fluid measurement procedure. During the fluid measurement procedure, the conductive bodily fluid forms a transient second plate-like electrode opposing at least a surface area portion of said first conductive plate; thereby facilitating an accurate electric, chemical or volumetric measurement procedure of the conductive bodily fluid. Typically the conductive bodily fluid forming the transient second plate-like electrode is channeled or being collected by another electrode 225 positioned so as to have a contact region with the conductive bodily fluid.

In some embodiments, the handheld integrated urine collection vessel is configured to provide fluid contact between urine and the at least one sensor.

The present invention further provides yet another handheld integrated collection vessel of a bodily fluid, comprising: a single use disposable receptacle for collection of a conductive bodily fluid comprising: inner and exterior side surfaces; and a bottom plate; the side surfaces comprise a dielectric substance and a first conductive plate is permanently coupled to at least a portion the exterior side surface so as to define a capacitive sensing volume within the receptacle and facing a surface area of the first conductive plate; the collection vessel is configured and operable to continuously collect and maintain the conductive bodily fluid in fluid contact with said inner side surface during a fluid measurement procedure. During the fluid measurement procedure, the conductive bodily fluid forms a transient second plate-like electrode opposing at least a surface area portion of said first conductive plate; thereby facilitating an accurate electric, chemical or volumetric measurement procedure of the conductive bodily fluid.

Capacitance of vessel is measured at first conductive plate and the second plate-like electrode. In one embodiment, the measured capacitance responds to the electric, chemical or physical property of the conductive bodily fluid. This can be achieved by utilization of slave circuitry configured and operable to electronically communicate the measurement of an electric, chemical or physical property of the urine to an external processing master unit.

In some embodiments, the conductive bodily fluid is urine.

The handheld integrated urine collection vessels can comprise a single use disposable urine funnel which capable of being removably fitted in the receptacle; the urine funnel have a top opening to receive the collected urine from the user and is aligned with the receptacle to facilitate urine passage into the receptacle; the disposable urine funnel forces the collected urine to be disposed horizontally and uniformally on the inner surface of the bottom plate; thereby achieving uniform fluid contact of urine with collection vessel inner side surface.

In some embodiments, the master circuit feeds the slave circuitry of the receptacle with power supply. The master circuit can produce signal(s) which control the slave circuit of the receptacle.

The sensor in the sensor assembly can be a capacitive-sensor and for example, the sensor can comprise a conductive plate which is used to define a sensing volume opposing at least surface area portion of the plate.

In some embodiments, the handheld integrated urine collection comprises a receptacle interface adaptor. The external processing master unit is removably attachable to the receptacle interface adaptor thereby facilitating electronic communication between the sensor and the external processing master unit.

The slave circuitry is configured and operable to continuously communicate plurality of said measurements to an external processing master unit.

In some embodiments, the master unit accumulates and determines the test results from said plurality of said measurement.

It should be noted that the specific embodiments provided herein are applicable to all urine collection vessels disclosed herein.

For urine flow measurements or tests, the present invention provides for a handheld disposable urine collection vessel; the disposable urine collection vessel includes walls defining a fluid volume, sensors which are permanently affixed on the walls (of side surfaces); and a communication adaptor such as 260 which allows transmission of the measured to an electronic recording device. The sensors affixed are designed for one or more uses. In some embodiments, the sensors are configured and operable for single use sensor.

The communication port (such as an interface or male/female plug component) is configured and operable to communicate with an external electronic device and to facilitate communication of the measured data from the sensors to the external electronic device.

In accordance with some embodiments of the present invention, the sensors are required to be durable during storage (e.g. being stored in fluid tight plastic seal). However, for use of the disposable urine collection vessel the seal is removed, the vessel is thereafter used and disposed off. Therefore, the importance of durability of the sensors and maintenance of the urine collection vessel and/or its sensors (or electrodes) is completely removed from consideration of the user.

Therefore, the present invention provides in some embodiments a single use handheld disposable urine collection vessel configured and operable to communicate with an electronic recording device. The electronic recording device can be in the form of portable or handheld device 100 (or 340).

A handheld device for recording urine measurements 100 or 340 is thus provided, the device is configured and adapted to electronically communicate with the handheld urine collection vessel disclosed herein; the device comprises the processing master unit to receive and process the measurement of an electric, chemical or physical property of the urine being obtained from the sensor or sensor plate; the device generates an output signal indicative of the urine measurement being performed which includes the results of the test or measurement.

Typically, the handheld device comprises memory component for recording the fluidic or urine measurements being performed.

In some embodiments, the device comprises a real-time clock; the device determine and accumulates plurality of separate urine measurements and associates them with time stamps being obtained from the real-time clock; thereby recording a 24 hour or more urine profile of a tested individual. Plurality of test results can be provided to the physician, the plurality of test being on a single time line.

The handheld electronic recording device can include a memory unit for storing the recorded data and data transferring means to transfer the measured data to a remote data processing and/or graphic visualizing device. The fluidic body sample can be crude or untreated body sample in a fluid form, as urine. The electronic recording device can be removably attachable to the disposable container so as to enable continuous and repeated use of the electronic recording device in combination with plurality of disposable fluid receptacles (for urine diary applications). Alternatively, the disposable container is fixedly attached to the electronic recording device and both are disposable and limited, by mechanical, electrical and/or any other way, for a single-use operation. In particular, the present invention provides for a disposable small container (or cup) for fluidic body sample which is electronically universal i.e. capable for allowing an electronic device to receive measured data being measured therein. In particular, the present invention also provides a USB CUP, disposable vessel (or cup) for fluidic body sample which permits communication of the measured data via a USB port.

In this way, a single electronic recording device can accumulate plurality of fluid measurements for later use while the disposable contained are, for example, being replaced or thrown away.

Thus, the present invention provides a multi-measurement electronic appliance which is ergonomic and can be removably attached to single use disposable vessel configured and operable to receive urine or another fluidic body sample and universally communication the measured data. In order to facilitate such practical functionally sensor assemblies requires special passive configuration discussed below.

Typically, the handheld device comprises memory component for recording the fluidic or urine measurements being performed.

In some embodiments, the device comprises a real-time clock; the device determine and accumulates plurality of separate urine measurements and associates them with time stamps being obtained from the real-time clock; thereby recording a 24 hour or more urine profile of a tested individual. Plurality of test results can be provided to the physician, the plurality of test being on a single time line.

Figure 8:
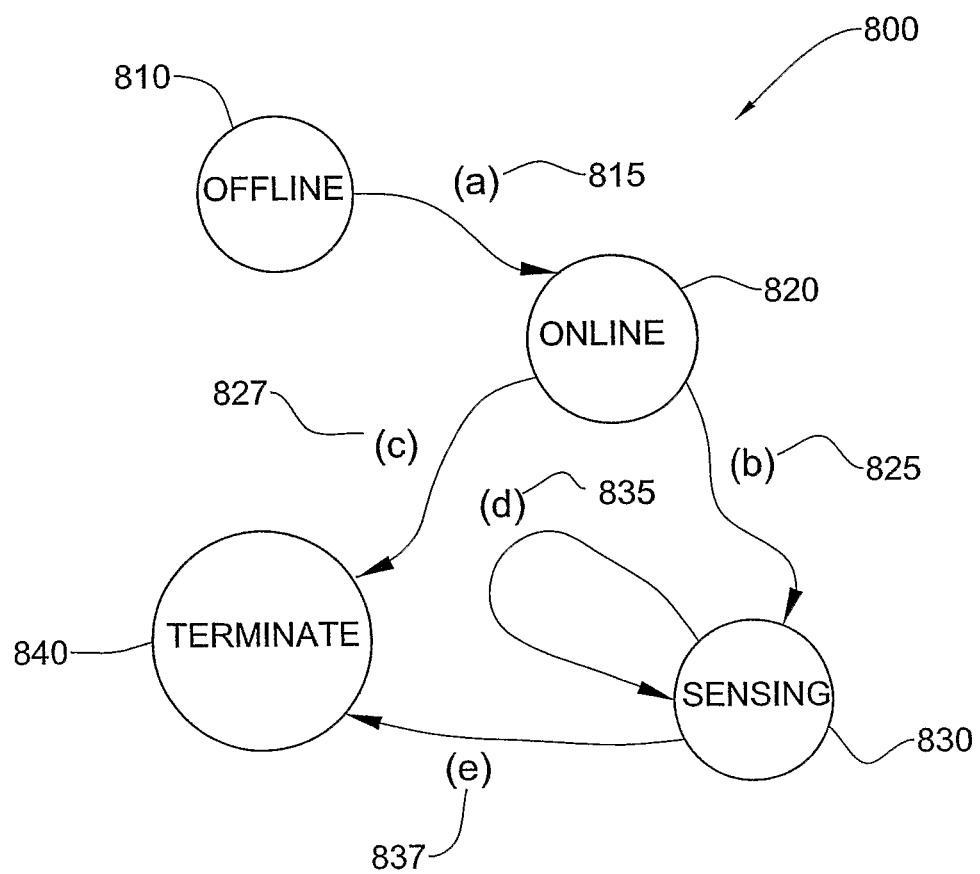
FIG. 8 shows a schematic machine state diagram of the electronic devices (handheld, stationary and dongle configurations) of the present invention.

FIG. 8 shows a schematic machine state diagram. The handheld electronic devices of the present invention used for recording the measurements and tests can be configured and operable to function or successively switch between several states as described in FIG. 8.

The electronic devices of the present invention can be configured and operable to have at least two states:

(i) an OFFLINE state 810 in which the handheld device is not in operable communication with the sensor; and (ii) an ONLINE state 820 in which the handheld device is in operable communication with the sensor; and The electronic devices of the present invention can further be configured and operable to have an additional SENSING state 830 in which the device is in operable communication with the sensor and communicating the measurements in real time. The schematic machine state diagram of FIG. 8 can be used in all devices and kits disclosed herein such as the stationary, handheld and dongle devices.

In some embodiments, the device can switch from the OFFLINE state 810 to the ONLINE state 820 following detection of a signal being received by a urine collection vessel being described herein. The signal can be received either wirelessly or via wiring connectable to an adaptor (e.g. 170) of the collection vessel. The switching 815 from the OFFLINE state 810 to the ONLINE state 820 is performed following verification of a sufficiently steady signal which characteristic of a physical ready to use condition of the collection vessel.

The device can switch from the ONLINE state 820 to the SENSING state 830 or TERMINATION state 840. The switching 827 from the ONLINE state 820 to the TERMINATION state 840 is performed if sensing cannot be performed. By way of non-limiting example, switching to TERMINATION state can follow detection of disconnection to the collection vessel from the device, or identification that the collection vessel being in communication with the device is reused in violation of a restrictive protocol enforced on the device or another rule enforcing single use routines. The single use protocol and other alike measures (or procedures) are provided herein below.

The switching 825 from the ONLINE state 820 to the SENSING state 830 is performed if sensing can be initiated or performed. By way of non-limiting example, switching to SENSING state 830 is actuated, following detection of a signal pattern being received from the collection vessel; said signal or pattern of signals is indicative of an initial sensing phase. For example, sensing phase can be initiated in conjunction with an increasing signal above a predetermined threshold, for a predetermined time window. The parameters such as the threshold and determination of the time window are predetermined by calibration procedures. During the SENSING state 830 the device continuous obtains 835 the measured input from the collection vessel and optionally records these measurements.

The switching 837 from the SENSING state 830 to the TERMINATION state 840 is performed if sensing cannot or should not be continued. For example, this occurs following reduction of the received signal below a predetermined threshold.

The device is removably attachable from the disposable urine receptacle, defining an attached configuration and a detached configuration. The device facilitates electronic communication between the sensor and the external processing master unit.

The processor unit can be configured and operable to receive and process measured data indicative of urine flow rate or urine volume.

In some embodiments, plurality of urine measurements is performed as a function of time. In some embodiments, urine measurements are transformed to qualitative parameter.

The device can be operative to exchange information relating to the urine measurement with a host controller of at least one of personal computer, remote computer or computer environment. The exchange information is typically facilitated by a USB connector interface. The information exchange can be facilitated by a wireless transmitter.

The device can include a real time clock providing a time stamp for the measured data obtained from the handheld urine collection vessel. Real time in this respect can be a clock capable of being set to the actual time so as to enable accurate time stamps for the test and measurements being performed.

The device can be connectible to an external memory utility for recording said urine measurements. The memory utility can be a removable Disk-on-Key memory device, USB stick, Multi-Media-Card (MMC), or an SD memory card.

The device can also operate as a stationary device for recording urine measurements. The device can thus be configured and adapted to electronically communicate with the handheld urine collection vessel disclosed herein.

The stationary device comprises a processing master unit to receive and process the measurement of an electric, chemical or physical property of the urine being obtained from the sensor. The device generates an output signal indicative of the urine measurement and can communicate the results of the measurement via electronic communication being selected from wired or wireless communication.

The stationary device for recording urine measurements optionally includes a printer for printing an output indicative of said urine measurement.

Whereas urine flow is measured by the sensor(s) of the disposable vessels of the present invention, the sensor(s) can track the level of liquids in the receptacle as a function of time. The stream of data is communicated to the electronic recording device which records or stores the measured data. Following the completion of the urine flow test or measurement, the detachable electronic device can be separated from the container, while still maintaining the information stored therein during a sensing phase. It is important to emphasis that the electronic measurement unit has the dimensions of a USB Disk on Key and can retains the data as a file for archiving like a regular Disk on Key.

In a one embodiment, the measurement can be read directly by a personal computer (PC) via the USB port, for example. In other embodiments, the urine measurement can be read by another dedicated reader.

The present invention further envisages an electronic recording device such that in an attached configuration can transmit or communicate the information (measured data) of the test via wire or cable. In other embodiments, the electronic device can transmit the measured information of the tests being performed via Wi-Fi (i.e. wireless means), Bluetooth, or Infra-Red, or other means to a PC or dedicated reader. In some embodiments, the device is configured to communicate with a Smartphone, a PDA and/or a web browser.

While the electronic device is a handheld device allowing use of the urine measurement device in the private setting it can still deliver the results to either local or remote computer environment.

The disposable container can be made from variety of durable materials. In particular, the disposable container can preferably be made of hardened paper, plastic or other suitable polymer preferably a disposable single use material.

The disposable urine collection vessel of the present invention can thus be a disposable plastic cup made of PET (PETP, Polyethylene terephthalate) and alike. Other plastic materials can also be used in the respect including PP (polypropylene), PS (Polystyrene), or PVC (Polyvinyl chloride). Biodegradable disposable material can also be used in this respect. Biodegradable plastic include, for example, polylactic acid based containers. Strong and firm shaped cups and containers are required for being used as the disposable collection vessel or container.

The handheld integrated urine collection vessel of the present invention is configured for "a single use". In this respect, the handheld integrated urine collection vessel of the present invention is designed to cease its functionality after being used once. In some embodiments, the device further includes a restrictive measuring protocol that permits only a single measurement performed with a disposable urine collection vessel thus preventing improper multiple utilization of the disposable vessel. The measuring protocol can be implemented by a security module or a software module which is executed by the device during testing (e.g. external master unit) to perform the restrictive measuring protocol. In some embodiments, the device identifies a change in the electrical or chemical property of the sensors deployed in the collection vessel. This change can be an electrical signature characterizing a sensor degradation following the performance of a continuous testing procedure (e.g. of about 5 minutes). In another embodiment, the collection vessel comprises an electrical component having a memory-like property. The memory-like property can record an electrical disabling mark; the mark is thereafter identifiable by the device so as to prevent further use In other embodiments, the disposable container (or vessel) comprises materials that facilitate rapid disintegration following a continuous contact with urine for about a period of about 5 minutes (or optionally about 10 minutes). The disposable container can for example comprise biodegradable material permitting the rapid disintegration. The material can thus be durable and resilient during testing and permit rapid disintegration in water/urine after use. It can comprise a plurality of layers of paper, binders and an absorbent material. The amount of absorbent material and the binder material selection can determine the disintegration rate of the disposable container upon contact. The disposable container's resilience and stiffness is determined to permit urine testing for about 5-10 minutes to ensure that the receptacle would not be re-used in a succession of urine measurement.

In some embodiments, the conductive plates can be fabricates on the side surfaces of the collection vessel. In other embodiments, conductive paint can also be used as a plate or sensor(s). The conductive paint typically is applied so as to provide sufficient sensing surface area.

For allowing urine flow measurements, these disposable collection vessel/cups normally should permit containing of about 11-18 oz of liquid and have top diameter of about 100 mm and bottom diameter of 70 mm bottom.

These fluid collection vessels can include a sensor assembly having permanently affixed sensor(s) which can be selected from liquid level/volume sensors. Capacity based sensors or capacitance sensor can be used to obtain liquid level measurements.

In some embodiments, the sensors are those which can detect (or measure) a substance or chemical constituent of the fluidic body sample and permit electronic conveyance of the measured data to the external master unit as described herein.

The sensors are permanently affixed to specific or special designated locations in the disposable fluid collection vessels.

In accordance with the disclosure of the present invention, the disposable collection vessel comprises a sensor assembly which the sensor(s) and passive electrical elements which enable communicating the measured data via passive means. The sensor assembly is permanently affixed on the disposable collection vessel. Thus, the sensor assembly is configured and operable to communicate the measured data from the sensors to the communication port installed in the disposable collection vessel. The communication port in turn permits receiving of the measure data by the electric recording device.

The sensor assembly preferably comprises passive or slave elements i.e. passive circuitry that does not include any kind of internal power source e.g. on board power source. "Passive circuitry" or "slave circuitry" shall mean an electric circuit which does not include any kind of internal power source. The sensor assembly of the present invention is being configured and operable to connect or be plugged/communicating with to a master circuit which provide power source to the passive circuitry. In a preferred embodiment of the present invention, a passive circuitry can include a coil, a capacitor or a resonance circuit and electric wiring (e.g. coupling these elements) to respond to presence of fluidic body sample or a constituent thereof. In other embodiments, the slave circuitry does not include either smart or processing unit(s). Therefore, control and processing can thus be provided by the master circuit which is being configured and operable to connect or be plugged/communicated to the sensor assembly.

The invention disclosed herein therefore provides for disposable sensor assembly and sensor elements. In this manner, following the completion of the fluid or urine measurement the disposable collection vessel is disposed together with the sensor elements alleviating the need of removing contaminant, washing or any preparation step. In addition, the disposable collection vessel disclosed herein permits for urine/fluid measurement or test which is based on actual contact between the sampled urine and the sensors without the need to maintain hygienic conditions to facilitate testing. This advantageous feature permits reliable fluid measurements which is, on one hand, not based on associating indirect properties of urine, such as, weigh of the liquid and on the other hand without maintenance steps typically required for such test devices.

It should be noted that devices which provide for fluid measurements e.g. urine flow measurements which base their test results on indirect properties of the measured liquid (weight, for example) are thus susceptible intentional or inadvertent intervention by users. This is substantially important for the private settings in which professional stuff are absent from and the user are not supervised. In addition, the disposable collection vessel comprise the sensors allows for urine measurement without complex moving parts or mechanical means such as scales.

In accordance with the teaching of the present invention, the disposable collection vessel comprises sensor assembly.

In some embodiments, the sensor assembly provides measurement and measured data relating to the liquid level in the vessel. The sensors which can be used can be the functionalities of linear liquid level monitors or calibrating sensors. In particular, the liquid level sensor can be based on resistance measurement using non-coated conducting plates. The liquid level sensor can also be based on capacitance measurement using coated or non-coated conducting plates. The sensors of the present invention can further be located at specific positions/heights in the urine collection vessel. In this manner, the sensors can provide an indication of liquid crossing a designated level or a plurality of such locations.

Where the sensor detects or measures chemical constituent of the fluidic body sample, the sensor can be selected from various chemical reactions to urine ingredients such as pH, and other which exhibit a change in color or other physical characteristics that is then translated to an electrical signal by the sensors.

In some embodiments, the disposable collection vessel comprises sensors of more than a single type to provide multiplicity of fluid measurements.

In some embodiments, the sensors are adapted in the vessel to provide information or measured data such as liquid level, conductance of the measured liquid (urine) or flow rate/volume. In some embodiments, the measure data is measured as function of time.

The electronic device for urine measurements of the present invention can be optionally an electronic recording device which records the fluid/urine measurement performed. Information or measurements can be recorded on a memory utility. At least one memory utility can be one of the following memory components: Volatile memory like SRAM/DRAM or Non-Volatile like Flash/USB memory stick. The electronic device can be a handheld or a portable device. It should be appreciated in this respect that the present invention provides for urine measurement apparatus having considerably reduced size. For example, the size can be in the range of 3-8 cm and more.

The handheld electronic device can be configured to removably attach and/or communicate with a memory utility such as a flash memory based utility. The handheld electronic device can be integrated with the memory utility. The memory utility employed is used as the media upon with the measured data is recorded. The handheld electronic device can communicate for example with a Disk-On-Key memory stick. The handheld electronic device can be a special Disk On Key. This allows the recordal or storage of the urine measurements for remote use in variety of the computer environments. Such use includes data analysis of the urine measurements.

The electronic device can comprise an interface which allows wireless communication with the sensor elements.

The electronic device also comprises an interface to allow wired communication with to personal computer (PC) or other computer environments. In this respect, the communication can utilize USB or RS232 protocols, for example. The electronic device can also allows wireless communication with the personal computer (PC), computer networks and alike. Wireless communication, in accordance with the present invention includes WiFi, Bluetooth or RF or other known wireless communication means.

The electronic device also comprises a processor unit configured and operable to receive measured data indicative of a urine measurement; the measured data is received from a sensor located at the disposable container.

Independent power supply can be provided to the electronic device. The electronic device can further comprise detachable other elements or portions, such as detachable power supply, memory utility or detachable interface adaptor.

FIG. 1A illustrates a schematic illustration of a kit 10 which comprises the electronic device 100 (shown in FIG. 1A in a detached configuration) and a urine/fluid collection vessel which comprises a receptacle 150. In the detached configuration, the handheld device for recording urine measurements (or electronic device) 100 is separated from the urine/fluid collection vessel 150. The receptacle defines an aperture 155 for allowing the collection of urine to be tested. The receptacle is made of material which is sufficiently durable to withstand urine collection, for example. To that end, it may optionally be coated with a protective layer. The protecting layer can provide sealant means for liquid control.

The receptacle can be made of hardened paper or from plastics. The receptacle also comprises side walls 160 and optionally a base or fluid impermeable bottom 165. The base can define an outlet or an orifice 167 to channel urine away from the receptacle. Optionally, the receptacle provides an interface adaptor 170 to provide communication between the sensor assembly and sensor(s) (e.g. permanently affixed onto the sidewalls of the receptacle) and the electronic device 100 positioned in the receptacle perimeter. In some embodiments, the electronic device 100 typically includes a plug 105 which can be removably coupled or attachable with the interface adaptor 170 from which measured data is electronically received. Plug 107 is used to allow connectivity to a PC and another computer environment system (e.g. computer network of the physician who ordered the performed measurement). The sensor(s) are not shown in FIG. 1A but will be further described and illustrated below.

Figure 1B:
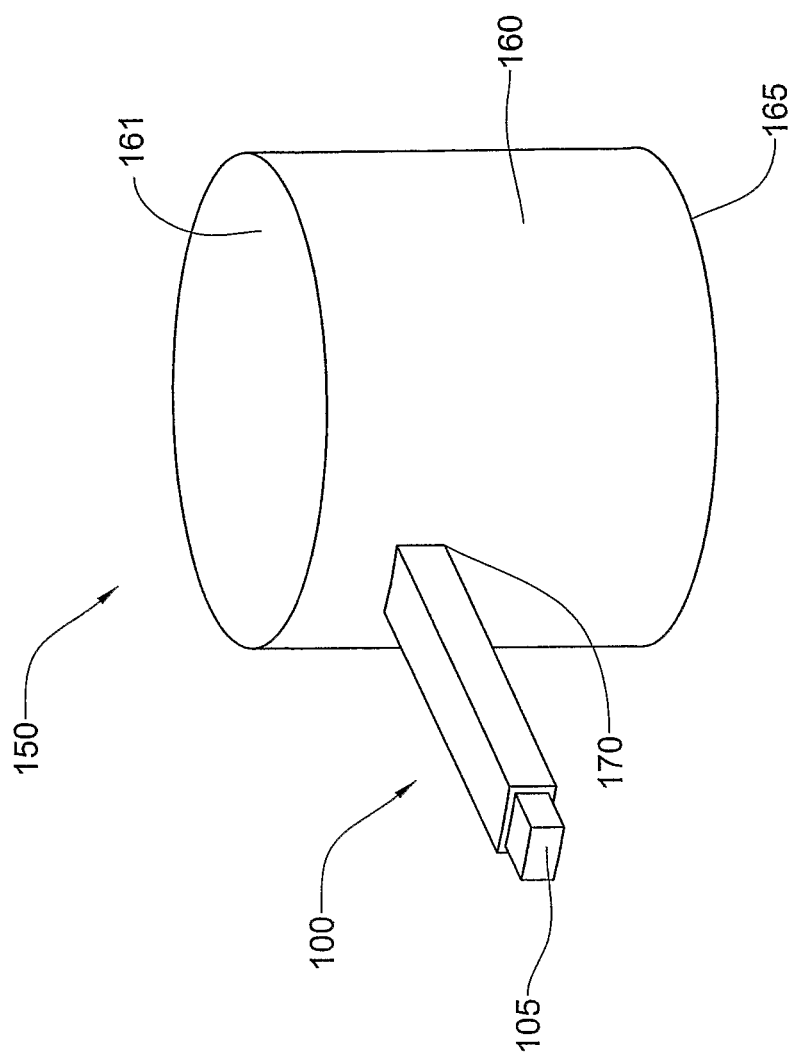

FIG. 1B illustrates a schematic illustration of the electronic device 100 of the present invention in an attached configuration. In the attached configuration, the electronic device 100 is physically connected to the urine container or vessel 150 (by wire through plug 105).

In FIG. 1B interface adaptor 170 permits direct communication between the sensor assembly and the electronic device 100 positioned in the vessel perimeter. As shown in the FIG. 1A-1B the present invention provides for considerable reduced size in comparison to the size of conventional urine measurements apparatus. In some embodiments, the present invention therefore provides for a urine measurement device having reduced dimensions. The overall length of the electric device or electric recording device can be as low as 20, 10, 7, or 5 cm. The overall length of the electric device in an attached configuration including the dimension of the disposable vessel can be less than 40, 30, 20, 17 or 15 cm. The width of the electric device ranges from 10, 5, 2, or 1 cm. The width of the disposable receptacle vessel can be less than 30, 20, 15 or 10 cm.

Figure 2A:
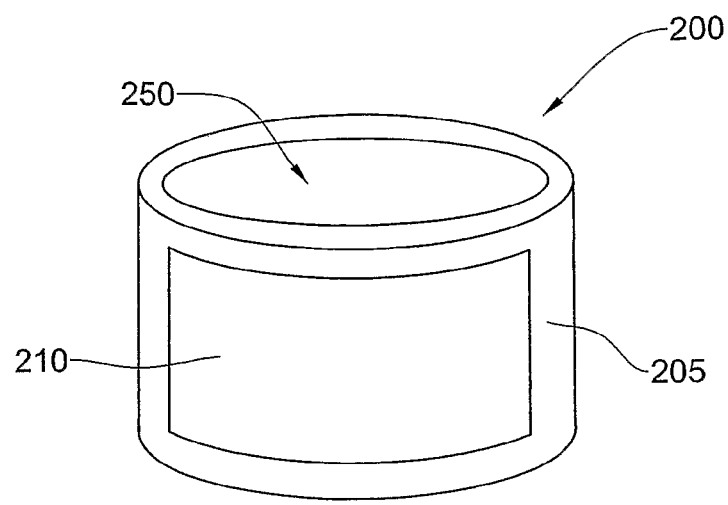
FIGS. 2A-2C.
Figure 2B:
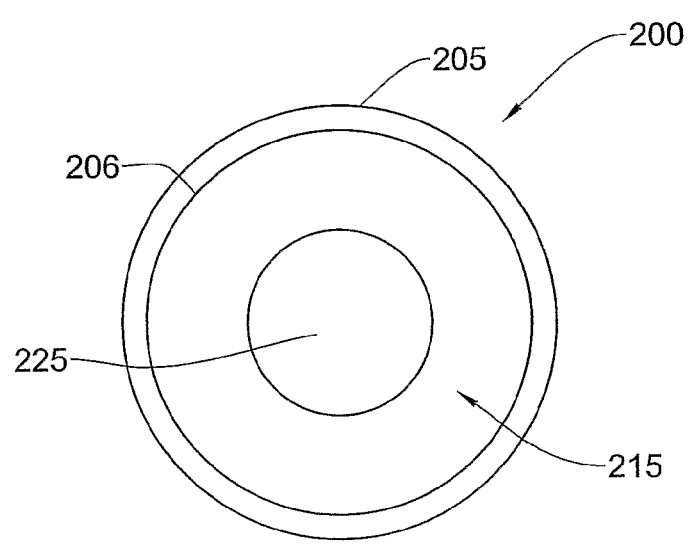
Figure 2C:
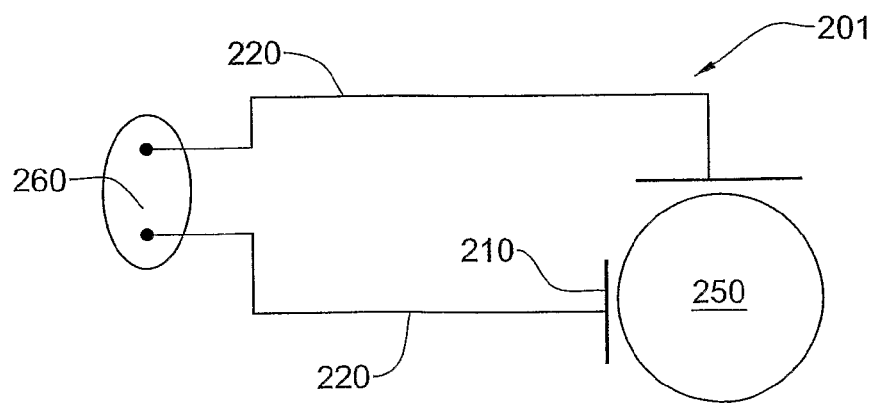

FIG. 2A-2C shows an exemplary urine collection receptacle 200 which is used for performing urine measurements such as urine flow measurements. The urine receptacle 200 is circular shaped and includes one or more insulated conductive plate 205 covering at least a portion of the side walls and permanently attached thereto. The surface area covering the portion of the sidewalls defines a volumetric sensing region 250 within the lumen of the urine collection vessel 200 facing said insulated conductive plate. The insulated conductive plate can be affixed to the external side walls of the receptacle (hence achieving insulation by the receptacle dielectric body). Alternatively or in addition, another conductive electrode can be covering a portion of the bottom wall (or plate) 215 of the urine receptacle 200. The bottom conductive electrode is used as a collector to induce voltage difference between the external plate and the liquid being collected in the volumetric sensing region 250. The collected fluid accumulated in vicinity of the insulated conductive plate forms a second plate-like effect which changes the capacitive properties of the collection vessel. The fact that the internal liquid is a conductive liquid makes it effectively the second plate of the capacitor.

In some embodiments, the disposable vessel comprises a single use disposable receptacle comprising side surfaces, a bottom plate and a single use disposable sensor assembly, the sensor assembly comprising at least one sensor. The disposable vessel can be used as a capacitive measuring unit during the obtaining of the urine flow measurement. Optionally, a side surface (a wall portion) of the receptacle serves as an electrically isolating substance (i.e., a "dielectric") permanently coupled on one side to a conductive plate (i.e., the first "conductor") and capable of being in contact at its other side with the urine (an electrically conductive liquid serving as the second "conductor", instead of a plate). These can be mutually referred to a "cup capacitor". As urine fills up during measurement its level rises. In response, the capacitance changes due to the change in urine volume which changes the surface area of the "cup capacitor". These capacitance changes can be used to measure urine flow rate. In some embodiments, the urine first serves to close the electric circuit, for example by reaching a minimal predetermined level, and after it is further accumulates it serves as an area changing capacitor.

FIG. 2C shows an exemplary embodiment of a sensing assembly 201 employing or including at least two conductive plates. The sensing assembly further includes wiring and an interface adaptor to communicate the measured data obtained at the sensor region. One of the conductive plates is positioned to cover a portion of the side walls of the receptacle 200. A collection electrode 225 is positioned so as to cover a portion of the bottom plate 215 of the receptacle.

Thus, in this exemplary embodiment, a three-dimensional sensing volume is being defined by the sensing plate.

In some embodiments, the conductive plates are made of aluminum such as aluminum foil. Wiring 220 can be used to connect the sensor plates to an adaptor 260 which in turn can communicate the electronic device of the present invention for further processing. This dual configuration (plate and electrode) embodiment exhibits accurate urine measurement with high degree of indifference to the horizontal angle of the receptacle. Accuracy of the measurement is further provided by ensuring that the whole bottom plate is uniformly distributed with the measured fluid (e.g. via funnel of structure and size as disclosed herein). Thus, the present invention provides an accurate and reliable urine measurement device which having minimal dimensions and accurate measurement applicable to the home environment.

The presence of liquid in the vicinity of the sensing volume defined by the plates results with varied capacitance of the plates represent by (C) in the below described circuit. Measuring capacitance between plates is a function of the receptacle dialectical properties, urine liquid height level which defines the plate's surface area of the plate. It should be noted that the relational between said parameters is represented in the formula.

$$C = K \cdot E_0 \cdot \frac{A}{D},$$

wherein C is capacitance of the conductive plates, k is a dielectric constant, and $E_0$ equals $8.854 \times 10^{-12}$, A is the overlapping area of sensor plates (urine liquid height) and D Distance between sensor plates (container width). In some embodiments, the handheld integrated urine collection vessel is configured and operable to electronically communicate the measurement of an electric or chemical property or physical of the urine for continuous analysis of the measured data to an external processing master unit. The measurement at the sensor(s)/sensor assembly is continuous monitored to deduce the testing results from a plurality of specific measurement as a function of time.

In some embodiments, the processing master unit of the present invention includes a 555 circuit commercially available. The 555 circuit is an integrated timer/oscillator circuit in a form an electric chip, commercially available from Philips. The combination of such frequency dependant components and the devices disclosed herein permits both accurate measurement and miniaturization of the measuring devices.

Figure 6A:
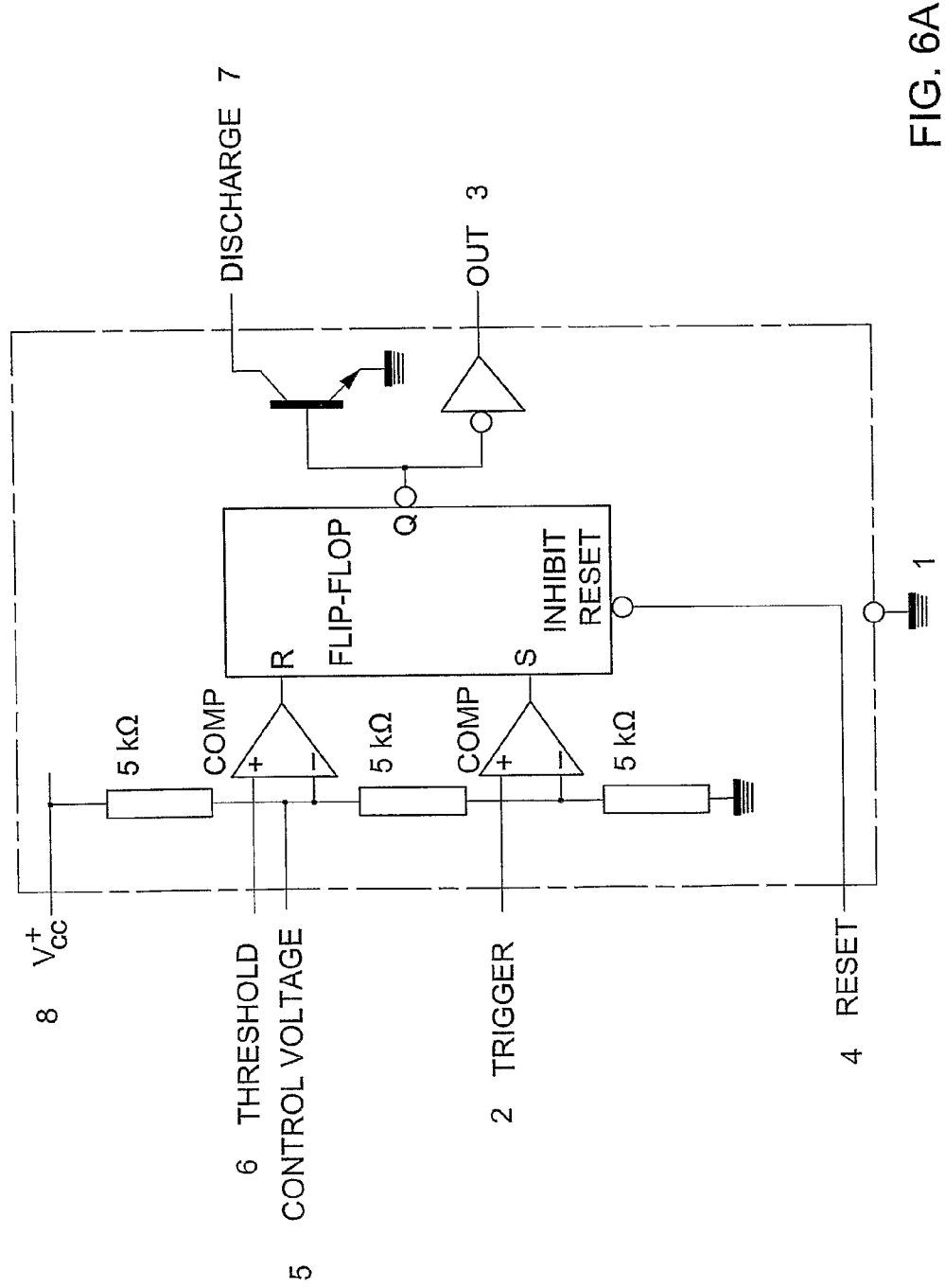
FIG. 6A-6B.
Figure 6B:
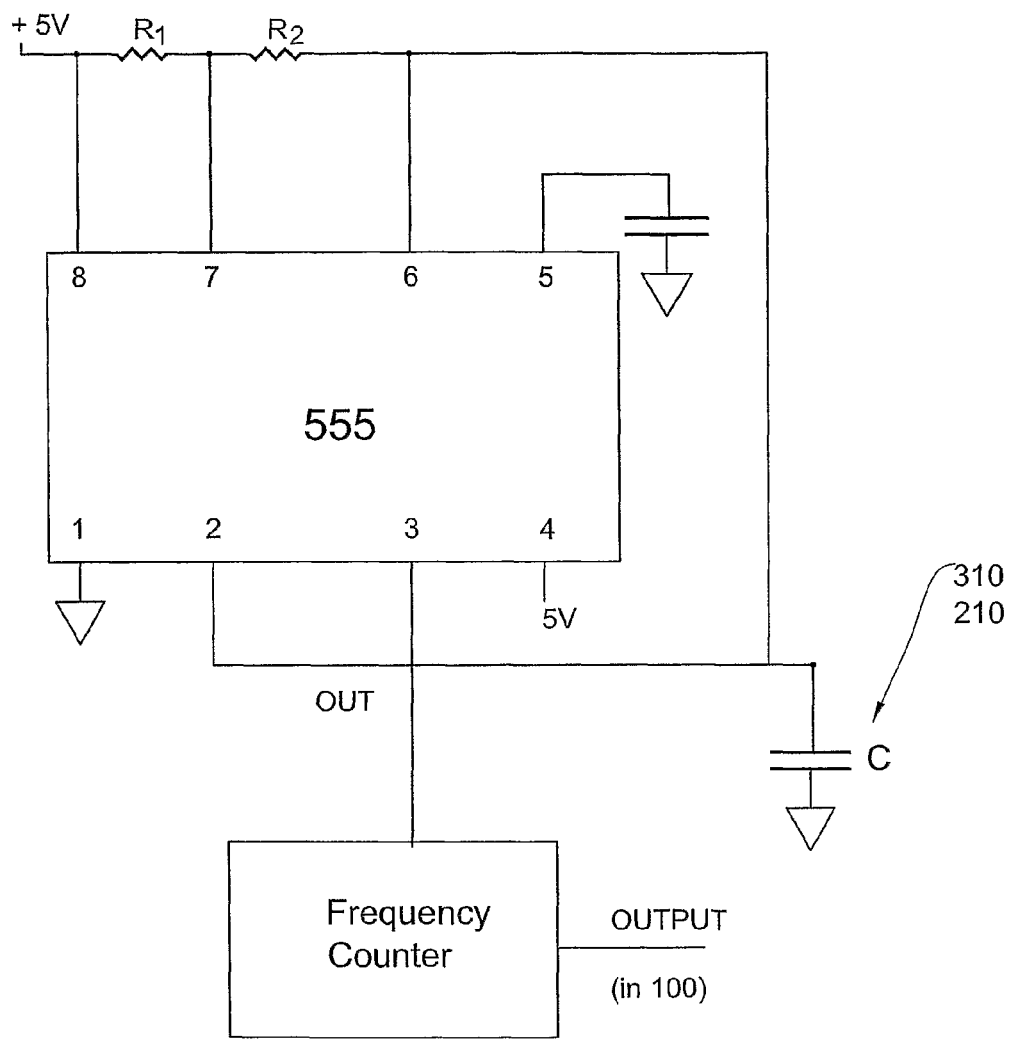

FIG. 6B shows an example of the 555 circuit being configured to receive measured data for analysis. The output of the 555 circuit is a signal of square waveform (pulse form) the frequency of which is can be dependent on capacitance. The number of pulses per a time unit (e.g. seconds) determines the frequency and thus the capacitance is obtainable there from. This is further elaborated below. The capacitor (C) can represent the capacitive role of the integrated urine collection vessel of the present invention. In some embodiment, the capacitance can be that formed at the collection vessel adaptor being coupled to the sensor assembly of the vessel. The 555 can thus used in the context of the present invention to transform the capacitance measured in the sensing region/volume to frequency. In this manner to provide a capacity measurement in correlation to a signal frequency outputted from for example the 555 circuit. As capacitance in the sensing region is directly affected by liquid contained in vicinity to the sensing region. The 555 provides an exemplary utilization in which the liquid content measured causes frequency changes in the output signal continuously as a function of time. The output signal can be transformed by the processor unit to volume/flow rate measurements. In this respect, it should be noted that the volume of the container or receptacle is known and precise.

The receptacle for the collection of urine can be manufactured in various shapes and volumes. The receptacle can be shaped as a cup, cylinder or a cone. It that end, the following definitions and formulas can apply: (i) $A=\pi r^2$ (circle area); (ii) $P=2\pi r$ (circle circumference); (iii) $V=A*h=\pi r^2 *h$ (cylinder volume), (iv) $P=2\pi r*h$ (lateral surface area);

$$V = \frac{\pi r^2 * h}{3} \text{(conical volume)}, \quad \text{(v)}$$

(vi) $A=\pi r(r+S)$ (conical surface area—the conical volume is more complex. I would recommend to delete all conical formulas), where $S=\sqrt{r_2+h^2}$ In some embodiments, the receptacle is shaped as a cylinder. Where a cylinder is used to collect and measure a fluidic body fluid the changes in fluid height results from changes in fluid volume. This can be illustrated in the following size dependency of cylindrical height and volume $$V = A*h = \pi r^2 *h \rightarrow h = \frac{V}{\pi r^2} \rightarrow \Delta h = \frac{\Delta V}{\pi r^2}. \quad \text{(viii)}$$

Additionally, size (capacitor plates area) dependency of cylindrical height and lateral surface area can be described as follows:

$$P = 2\pi r * h \rightarrow \Delta P = 2\pi r * \Delta h \rightarrow \Delta P = 2\pi r * \frac{\Delta V}{\pi r^2} = \frac{2\Delta V}{r}. \quad \text{(ix)}$$

In some embodiments, measurement of an electric or chemical property of the urine is used to determined urine flow rate. Urine flow rate can thus be measured in accordance with changes in the capacitance of fluid accumulating in the receptacle. From the capacitance changes of the fluid accumulating in the receptacle lumen, the corresponding volume changes of the accumulating fluid can be determined.

Specifically the volume changes can be derived from the following dependency.

$$\Delta C = \frac{\varepsilon_0 \varepsilon_R \Delta A}{D} = \frac{\varepsilon_0 \varepsilon_R}{D} \frac{2\Delta V}{r} \quad \text{(x)}$$

The 555 circuit can be used to convert the changes in capacitance measured in the receptacle to frequency from which the test results can be obtained. For example the 555 circuit provides the following dependency between the frequency and capacitance. $C_1$ represent the capacitance measured at the receptacle or vessel. Resistors, $R_1$ and $R_2$ are selected and adjusted at the required resistance and thus can act as numeric constants during determination of the flow rate as derived from the frequency/wave length changes of the output signal in the 555 circuit.

$$f = \frac{1.44}{(R_1 + 2R_2)C_1},$$

and thus $$T = \frac{1}{f} = 0.693*(R_1 + 2R_2)C_1 \quad \text{(xi)}$$

By utilizing the 555 circuit, changes in the wave length frequency corresponds to changes in the volume of the fluid accumulating in the receptacle. The below dependency is derived from (x) above.

$$\Delta T = 0.693*(R_1 + 2R_2)\Delta C \quad \text{(xii)}$$
$$= 0.693*(R_1 + 2R_2)\frac{\varepsilon_0 \varepsilon_R \Delta A}{D} =$$
$$= 0.693*(R_1 + 2R_2)\frac{\varepsilon_0 \varepsilon_R}{D}\frac{2\Delta V}{r}$$

$$\Delta V = \Delta T * \frac{D*r}{2*0.693(R_1 + 2R_2)\varepsilon_0 \varepsilon_R} \quad \text{(xiii)}$$

Figure 9:
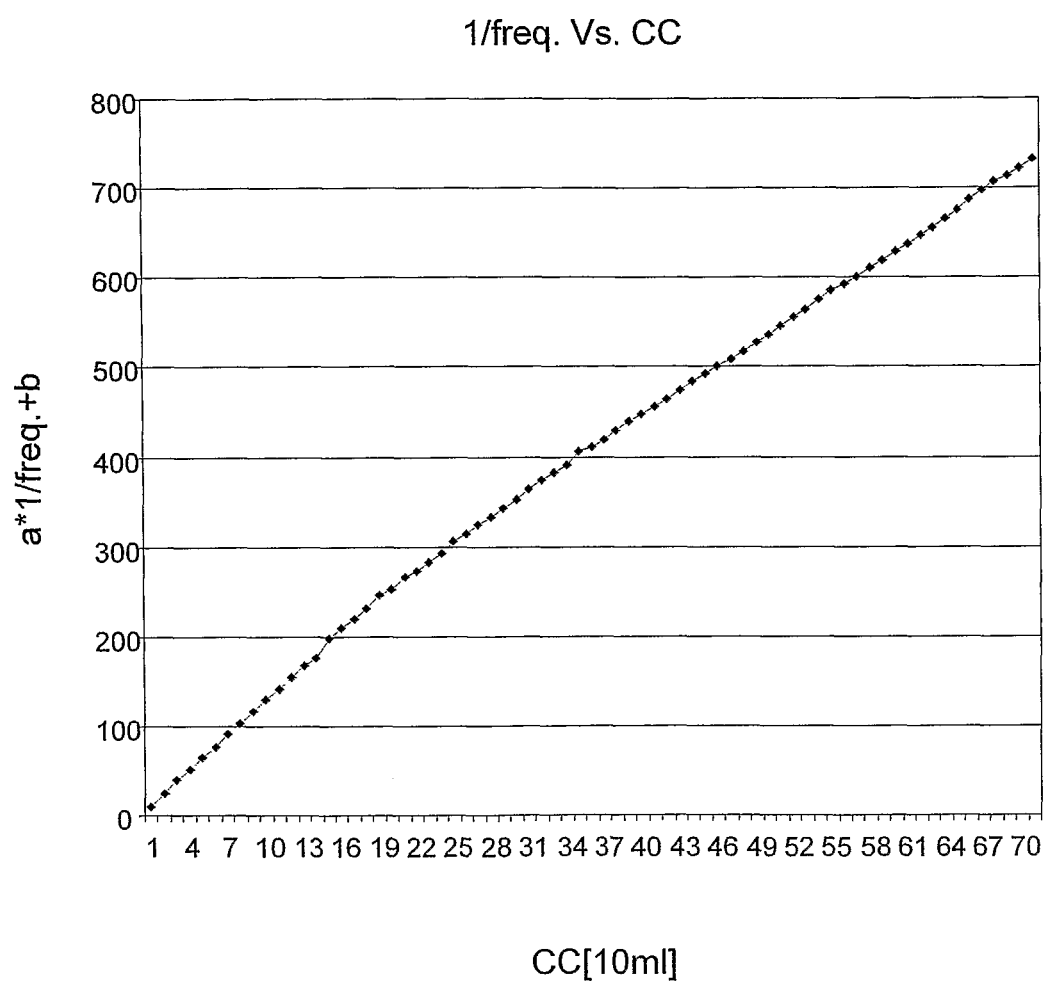
FIG. 9 shows a graph illustrating volume vs. frequency measurements of the electronic devices and vessels of the present invention.

FIG. 9 shows a graph illustrating volume vs. frequency measurements in accordance with the above. Thus, frequency determined by the electronic devices and vessels of the present invention exhibits accuracy and linear (or almost linear) dependency with sensed liquid volume tested. This property can be used in volume/flow rate measurements and other frequency dependant tests i.e. test that involve or are capable of being determined in accordance with frequency responsiveness.

The fluid rate can thus be obtained by determining the volumetric changes $\Delta V$ over time. In addition, the calibrating slope of volume and output signal wave length can be derived from:

$$\frac{\Delta T}{\Delta V} = 0.693*(R_1 + 2R_2)\frac{\varepsilon_0 \varepsilon_R}{D}\frac{2}{r} \quad \text{(xiv)}$$

In some embodiments, the receptacle can have other shapes such as a cone shape, or any axisymmetric or any irregular shape.

The output signal of the 555 circuit or another capacitance dependant circuit is fed into the electronic device of the present invention for further processing. In some embodiments, the electronic device comprises both capacitance dependant circuit (e.g. the 555 circuit) and the processor unit.

It is thus further provided a method for determining fluid rate in a fluid collection vessel, comprising:
identifying whether the fluid collection vessel is electronically communicating with an external processing master unit; the external processing master unit can be any electronic device of the present invention such as the handheld, stationary or dongle device.
determining if the device can switch to an ONLINE state in which the device is in operable communication with the sensor assembly of the fluid collection vessel (e.g. urine).
continuously obtaining measurements along a time line comprising at least one time window being defined as $\Delta T$.
determining the volumetric changes $\Delta V$ over time.

If some embodiments, the method further comprises determining flow rate according to the $\Delta T$ and $\Delta V$.

Any of the electronic devices of the present invention can be configured and operable to perform the method for determining fluid rate in a fluid collection vessel. In some embodiments, the handheld device for recording urine measurements comprises the processor unit which analyses the input feed to decide a urine measurement test results. The processor unit typically comprises a CPU or another data master processing circuit; and a memory interface to allow operation in conjunction with a memory utility and a real time clock. Memory utility typically comprises flash based memory devices.

The memory device can optionally store a computer program and operates the processing unit to execute the software code to perform urine measurement or flow test analysis. The interface can be a USB interface. The processor unit typically comprises an analog to digital (A/D) converter for transforming the measured analog data or a derivative therefrom to a digital form to be processed by the processor unit.

Optionally, Random Access Memory (RAM) is also provided to the processing unit. RAM can be used to store the executable computer program or code discussed above. The electronic device is also coupled to a power source to allow operability during the performance of the urine measurements. The CPU is configured and operable to allow control functions and communication based functions. Communication includes either recording the urine measurement/results on the memory utility or obtaining the measurement from the sensors and optionally to wirelessly communicate with a remote point of access.

Figure 3A:
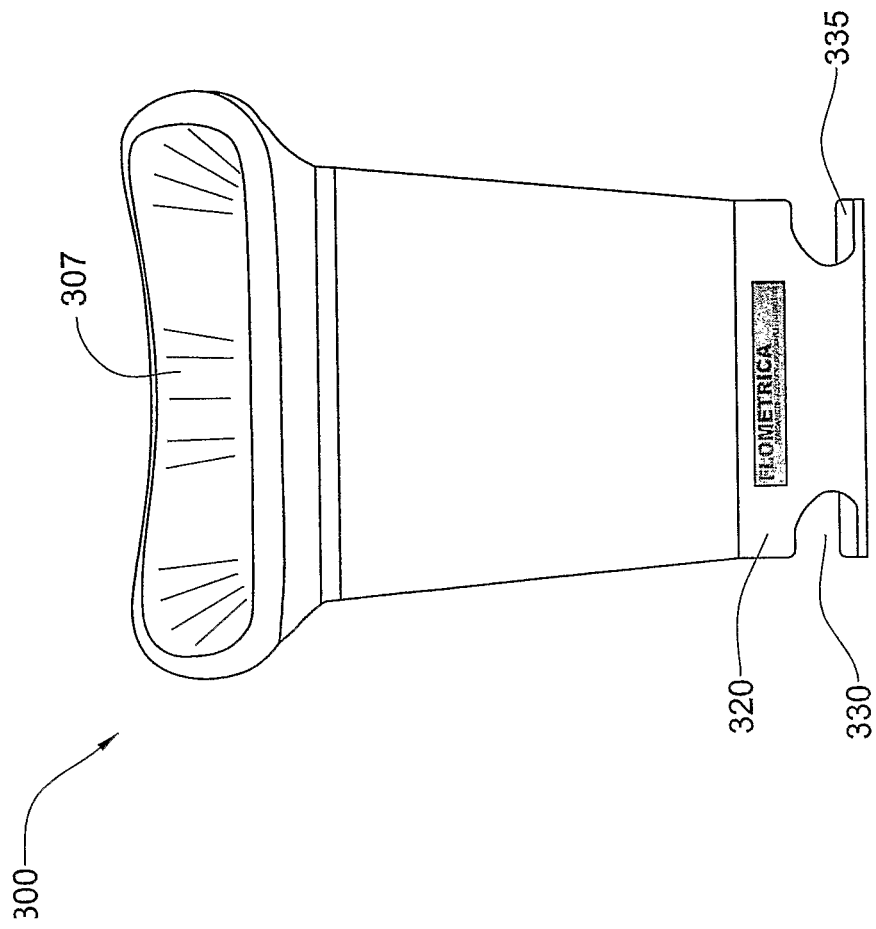
FIGS. 3A-3F.
Figure 3B:
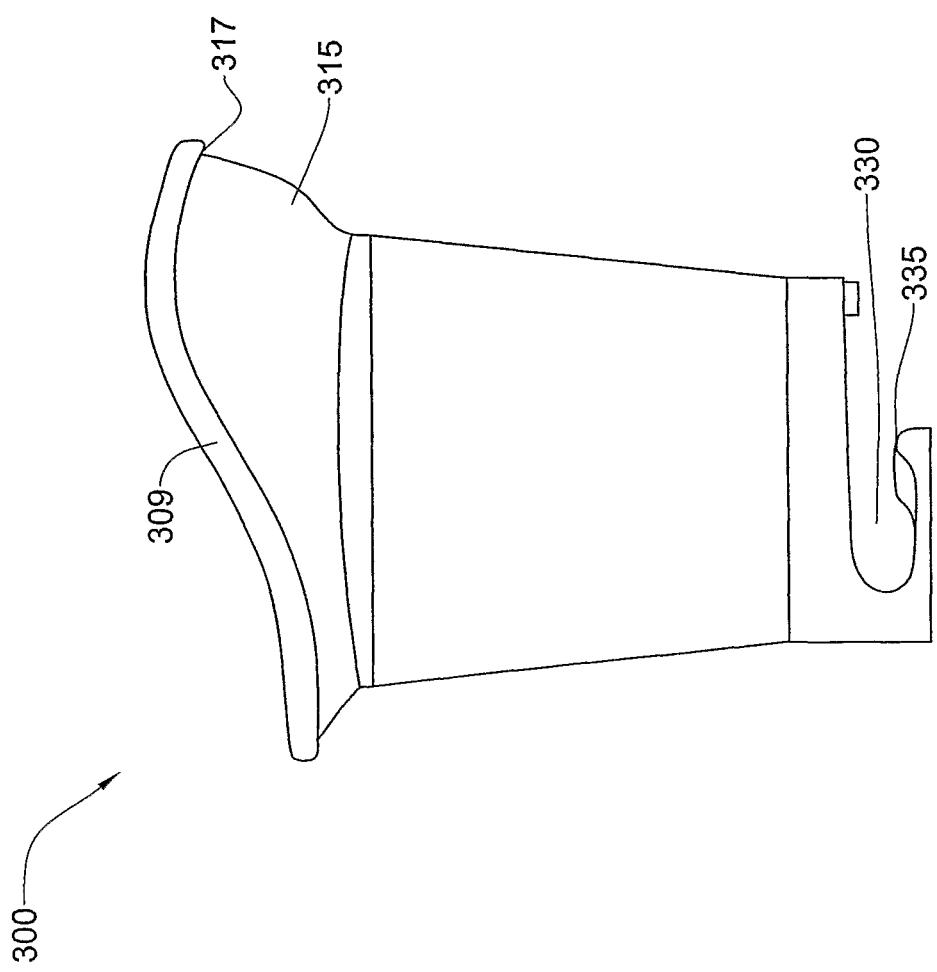
Figure 3C:
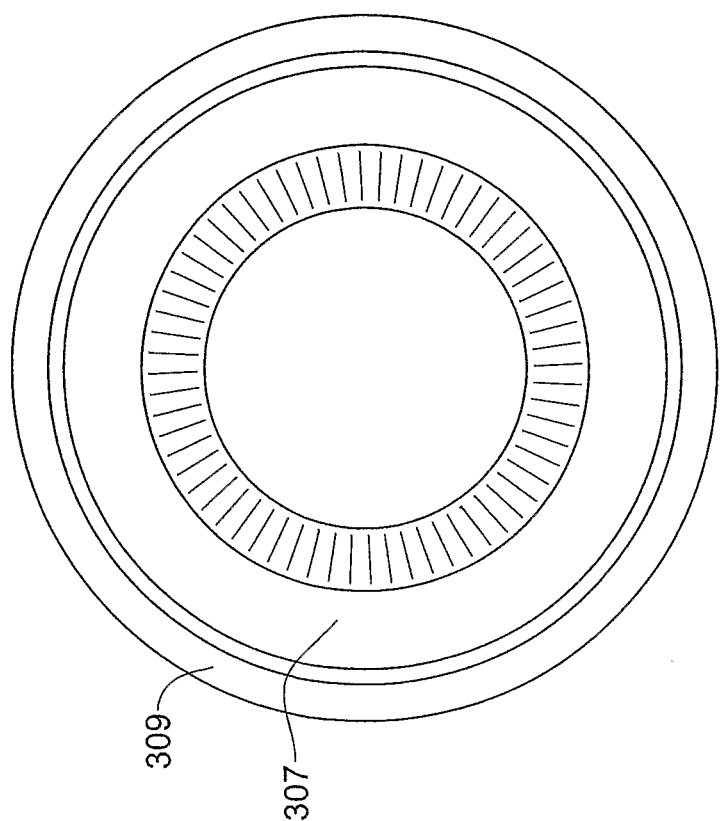
Figure 3D:
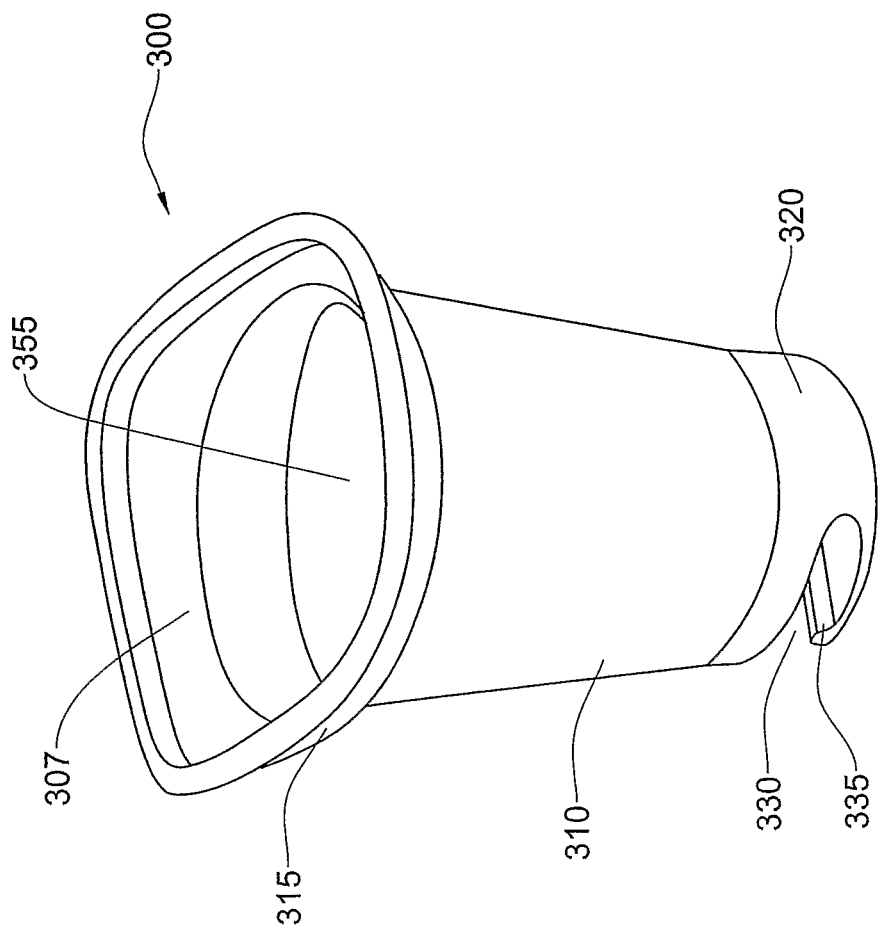

FIG. 3A is a side isometric view of another non-limiting example of a fluid collection vessel or vessel assembly 300; FIG. 3B is a side view of the vessel and FIG. 3C is a top view of the same. FIG. 3D is an isometric view of the vessel 300. As shown the vessel 300 can be of a circular-like shape. The vessel 300 can be also adapted and configured with to collect urine by use of a funnel 307. The funnel 307 can be a funnel shaped cylindrical member which collects a fluidic body sample. The funnel 307 can include a curved or contoured lip or rim 309 to allow convenient fluid collection while the vessel is vertically positioned.

The vessel 300 has also exterior side surface 310 and inner side surface 311 and optionally a cone-like shape extended portion 315. The cone-like shape portion 315 typically has a circumferential end 317 to receive the contoured lip or rim 309 of funnel. In some embodiments, the side walls (or surfaces) are made of conductive material which act as the conductive plate as discussed herein. In other embodiments, the sidewalls 310 are made of a non-conductive material and have a fabricated conductive plate covering a portion of the circumference of its sidewalls. The portion carrying the conductive plated should have a sufficiently wide surface area to permit the fluid measurement.

In some embodiments, the funnel 307 is removably fitted within the volume defined the sidewalls 310, as shown in FIG. 3D. Prior to use the funnel 307 may be in a removed or disassembled configuration (not shown). In other embodiments, variety of funnels can be fitted in the within the volume defined the sidewalls 310 in accordance with the needs of the user such as his height and the particular test applied.

The funnel 307 is typically made of hardened paper or plastic. The funnel 307 is a disposable container which can be made of PET (PETP, Polyethylene terephthalate) and alike. Other plastic materials can also be used in the respect including PP (polypropylene), PS (Polystyrene), or PVC (Polyvinyl chloride). Biodegradable disposable material can also be used. Biodegradable plastic include, for example, polylactic acid based, funnel shaped, vessels. A collector electrode 366 is typically provided and positioned about the bottom plate 365 of the fluid receptacle. The fluid pouring through the funnel is collected and accumulates in the receptacle and functions (during testing) as a second plate-like member gradually affecting the electrical properties measured at the receptacle. For example, the capacitance measured a first level of fluid varies in comparison to a second fluid level being collected by the receptacle.

Figure 4A:
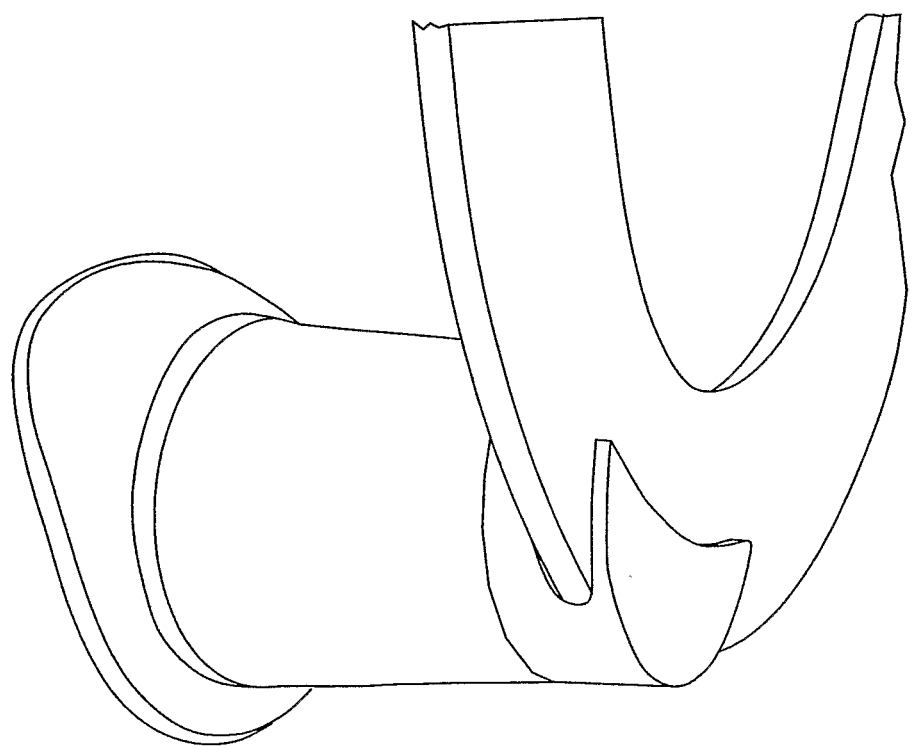
FIGS. 4A-4B.
Figure 4B:
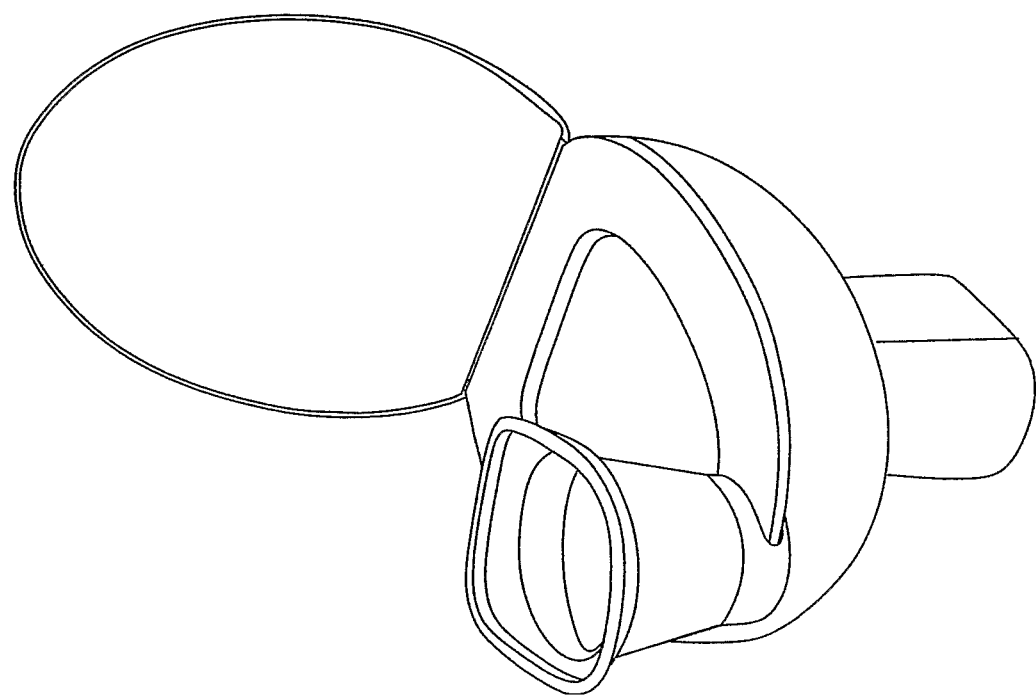

The vessel 300 also includes a base housing 320 which serves for physical support of the vessel while being in use. The base 320 have a groove 330 and a projecting member 335 to forcibly bias the vessel to a steady state during testing. The groove 330 and the projecting member 335 are configured in shape and size to receive a portion of a conventional toilet seat, functionality demonstrated in FIGS. 4A and 4B. Thus, the conventional toilet seat typically has a loop and circular flat cross-section capable of being accepted within the groove 330. This configuration permits stable positioning for the vessel 300 during testing.

Figure 3E:
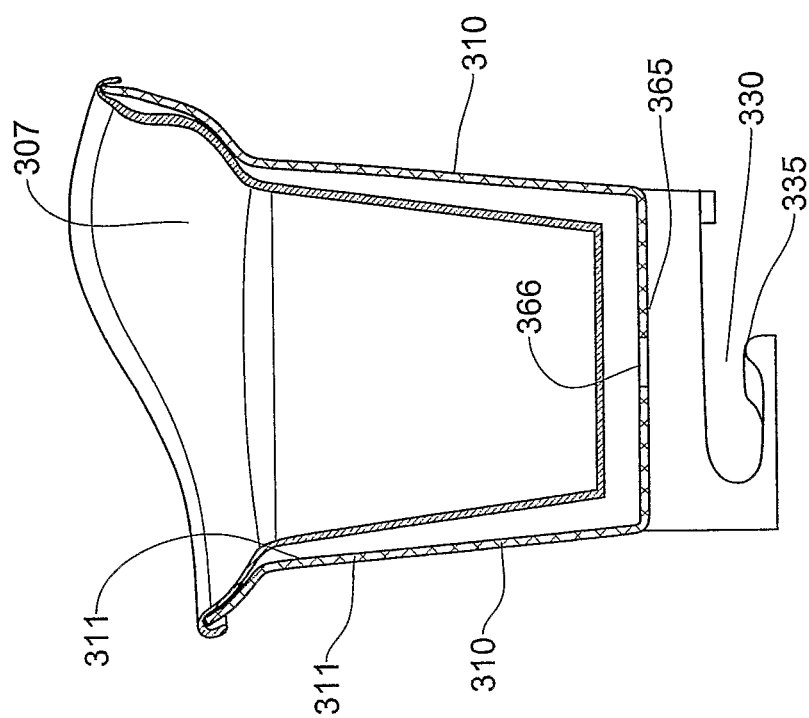
Figure 3F:
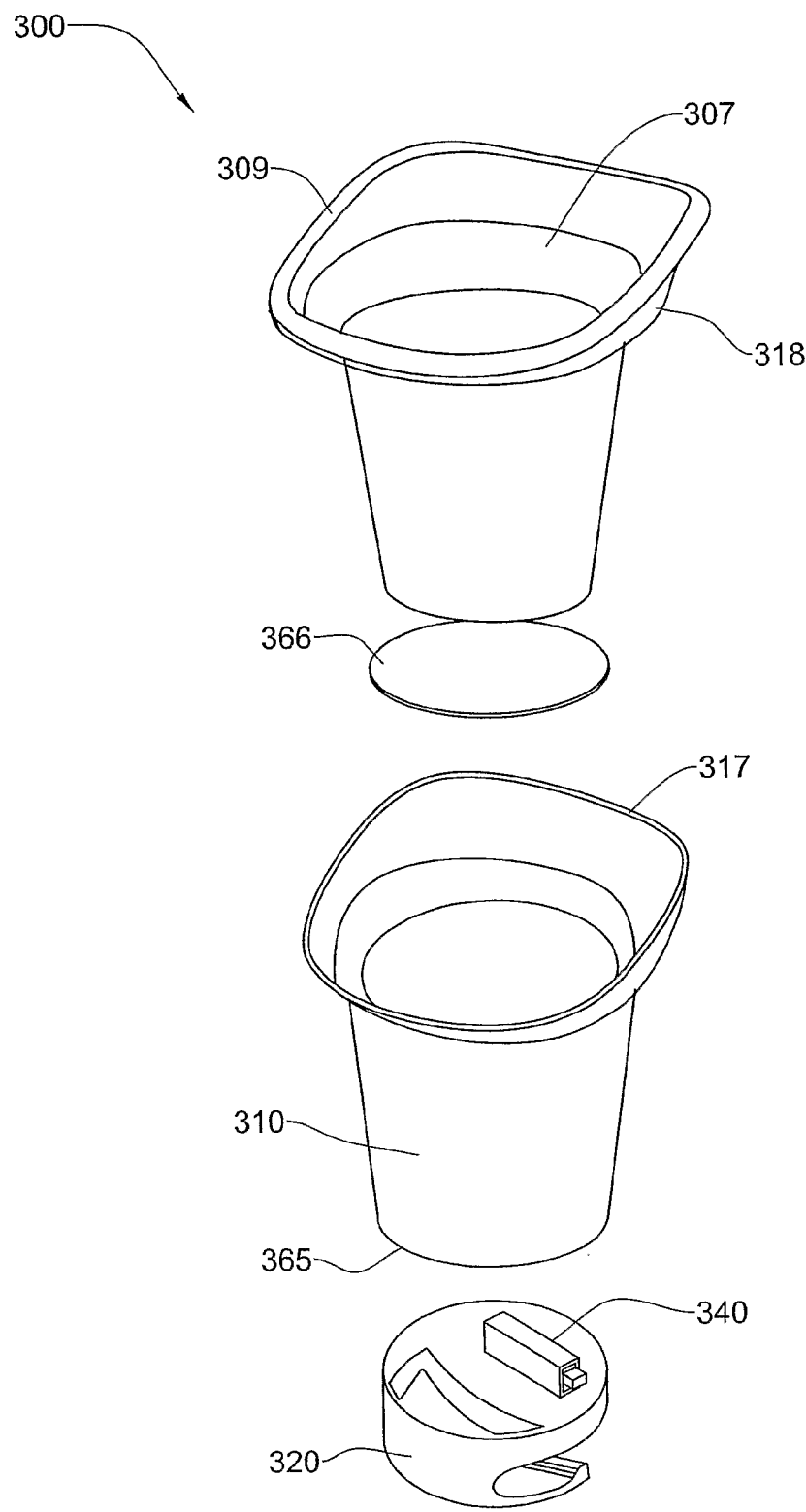

FIG. 3E is a side cross-sectional view of the exemplary fluid receptacle; and FIG. 3F is an exploded view of the exemplary fluid vessel. The funnel 307 conical shaped wall 308 and laterally extended portion 318.

Typically, the base housing 320 maintains an electronic recording device 340 in fluid free compartment. The electric device 340 can be permanently affixed to the base by an adhesive agent or a receiving element (not shown). The electronic device typically has a USB port to allow data connectivity in a computer environment.

This interface adaptor provides connection with the sensors deployed in the receptacle. The connection can be actuated for example by plugging the electronic device (e.g. via 107) into the interface adaptor. In one option, the electric device has a port such as a USB port 107 for allowing establishing communication between the electric device and for example an auxiliary memory utility which may be a Disk-on-key apparatus. In other embodiments, the electronic device is a Disk on Key apparatus or a dongle permitting communication between the device and a computer environment. The electronic device can thus be integrated and include a USB port connectivity. The electronic device can be integrated with a Disk on Key apparatus. The auxiliary memory utility typically has a USB male adaptor 172 providing connection with the female USB port for example in a personal computer of other computer environment.

Illustration of usage of electronic device 100 is now provided. In the following example, the electronic device in combination with a urine collection vessel of the invention urine flow is provided. The electronic device 100 can thus be operable with the disposable urine collection vessel e.g. vessel 150, 200 or 300. Prior to use, the vessel is typically positioned vertically with respect to a horizontal plane. This position is convenient for use by male users. A conventional toilet seat in a lower position can provide support for the collection vessel and maintain the vessel in a vertical position.

For female user the collection vessel can be configured and adapted to be positioned at least in part inside the toilet. Urine collection is thus enabled while the user sits on the toilet seat and deposits the urine sample in the collection vessel which is located below the urinary orifice of user and at least partially below the toilet seat. To that end the collection vessel can be laterally supported by plastic or elastomeric support arms.

Following the positioning the collection vessel, urine is collected from the upper portion of the vessel such as 155 or 355 shown in FIGS. 1 and 2. The user or patient directs the urine flow into the vessel. The urine can continuously contact the sensors while filling the collection vessel (not shown). In another configuration, urine fills a volume in close vicinity with respect to the sensors so as to affect the electrical properties of the sensors and thus enable the test.

Following the completion of a recording phase, the memory utility can be removed from the collection vessel. The disposable collection vessel used could be disposed without the need to restore it function or hygienic condition.

By obtaining the level/volume of liquid at different points in time, flow rate measurement can be determined. Urine measurement such as flow rate of the liquid received is measured and recorded on a memory utility such as a USB stick or a micro flash memory card. This allows easy access by the physician who will analyze the urine measurement obtained.

The memory utility can be also used to save the results of the urine measurement on a personal computer and optional electronically transmit the result to a remote location. Also, in the scope of the present invention a wireless configuration (not shown) in which the electronic device is coupled with wireless communication means. In the wireless configuration the urine measurement can be transmitted to a remote location such as a person computer nearby or another computer network employed for this matter. In some embodiments, a portable memory utility such as a Disc-on-Key apparatus is connected to a printer to directly print the urine measurement. When connected to a PC or a printer, patient test data can be plotted.

The urine measurements performed can include the following parameters and information:

(1) Urine flow graphs including volume vs. time graphs and flow rate (typically in ml/s) vs. time;
(2) Tdelay—Delay time until urination starts;
(3) T100—Voiding Time which refers to the total time during tested urination;
(4) TQ—Flow Time which accounts for the net time urine was added (not including breaks);
(5) Tqmax—Time to max Flow which refers to the time measure for the initiation of the urination until the time maximum rate is exhibited;
(6) Qmax—Max Flow Rate;
(7) Qave—Average Flow Rate
(8) Vcomp—Voided Volume, the total liquid flown thought the measurement device during the test.

Providing an accurate urine measurement device operable at home may require the ability to take into account the horizontal angle of said receptacle in relation to a horizontal plane. This horizontal angle is capable of influencing the urine measurement taken. In particular, it can affect the volume and urine flow measurements. Horizontal angle is compensated by the circular shape of the receptacle.

In some embodiments, the handheld electronic device 100 therefore can comprise a processor unit which is operable to transforms a liquid level measurement to an indication of the horizontal angle of the receptacle in relation to a horizontal plane. The angle of the liquid collected is determined from the differential reading of the respective sensors. The flow measurement can be thus performed taking into account the horizontal angle.

As used herein the term "insensitive/indifference to the horizontal angle" refers to the ability of the vessel to tolerate horizontal angle variations during testing".

The present invention provides a disposable urine collection vessel which allows accurate urine measurements which are not sensitive to the horizontal angle in which the receptacle is positioned during testing. In other words, the disposable urine collection vessel of the present invention can tolerate horizontal angle variations during testing. Horizontal angle of the receptacle in relation to a horizontal plane can be determined by a usage of plurality of sensors. The higher differential readings obtained from the sensors the higher the angle. As a result, accuracy of the measurement is reduced. The handheld electronic device can alarm the user in that respect.

In another embodiment, the sensors are configured and operable to obtain liquid measurement which is substantially indifferent to a range of an acceptable horizontal angle allowed. Also, adding some water at the beginning of the test will cancel all horizontal misalignments.

Figure 5:
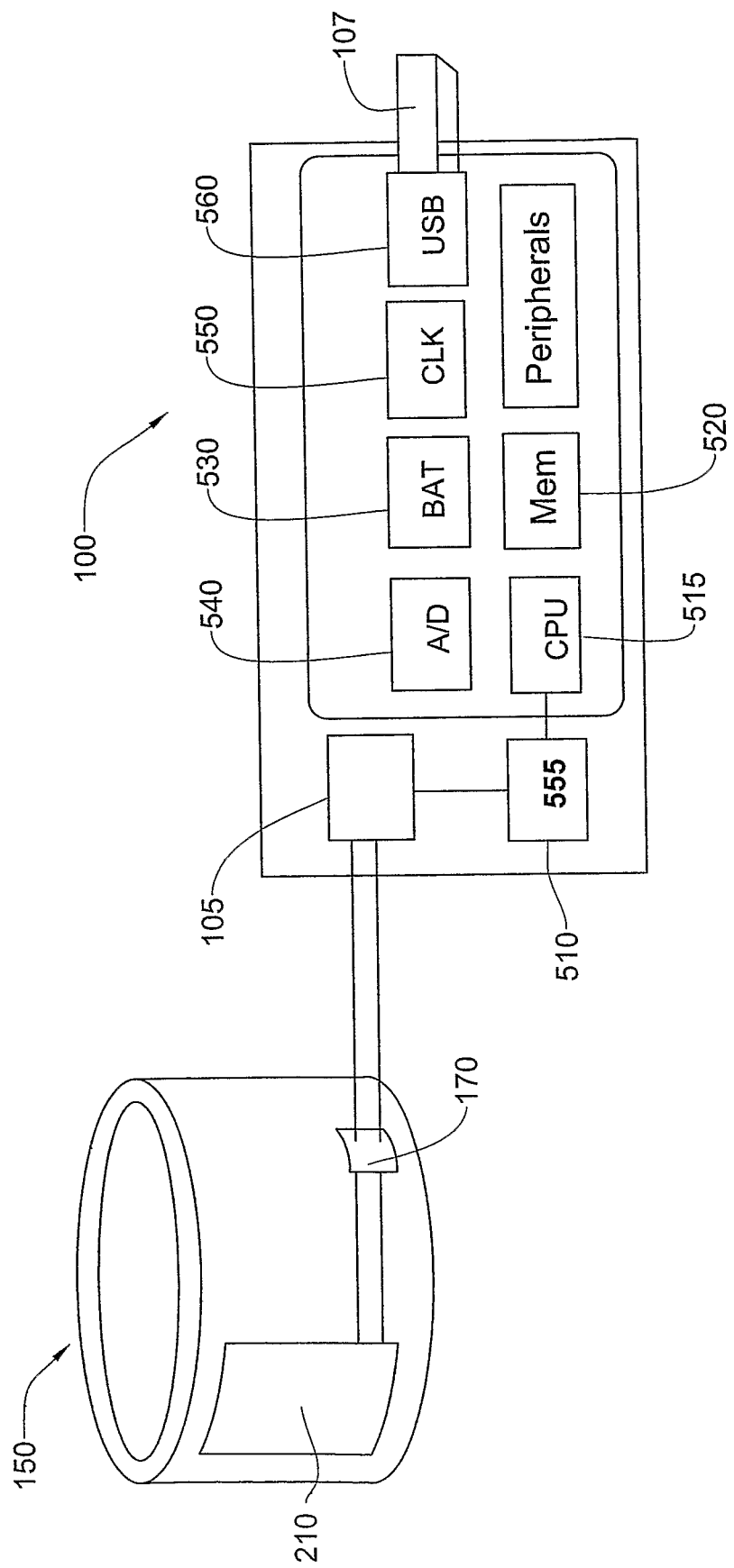
FIG. 5 is a schematic of the wiring from a fluid vessel to the electronic device for recording the measurements.

FIG. 5 is a schematic of the wiring from a disposable fluid vessel 150 to the electronic dongle device for recording the measurements 100. The disposable fluid vessel 150 is in the form of a circle shaped cup having an interface or a cup interface 170. The cup is electrically coupled and communicates with the electronic device for recording the measurements 100 by electric interface 105. For flow and fluid volume measurements such as urine measurement, electronic device 100 comprises a 555 circuit or other capacitive dependant element 510 which transforms changes in capacitance measured in the cup to frequency analyzed by the CPU 515 or another signal processor. Electronic device 100 can also include a memory component which can be selected from volatile to non-volatile memory elements 520 and an A/D convertor 540 which can be used to transform an analog measured signal or a derivative thereof. As previously described, the cup 150 comprises a permanently affixed sensor assembly having passive circuitry being responsive to the electric, chemical or otherwise physical properties of the measured fluid. The sensor assembly is supplied with an external power source 530. The electronic dongle device 100 can further include an electronic internal clock 550 providing the fluid measurement a reliable time stamp thereby providing a logical pair <measurement, timestamp>. USB interface component 560 permit connectivity to a personal computer or a computer network.

The electronic device 100, methods and kits of the present of the present invention provides for personalized urine measurement which can be easily obtained in the home settings. The invention provides for an accurate urine measurement device having substantially reduced dimensions and in part disposable and hygiene. It thus allows for patient privacy during testing while allowing accurate testing.

A hardware dongle device for providing a 24 hour urination diary is also provided herein. The dongle device comprises a master processing unit such as unit 100, a frequency dependent component responsive to an electric or other property of a measured data. The frequency dependent component can be responsive to a capacitive based component such as capacitor sensor being disposed in a volumetric sensing area. The dongle device can further comprise memory component, an electric interface, real-time clock, and a communication port.

The dongle device is configured and adapted to electronically communicate, receive and process an external measurement of an electric, chemical or physical property of the urine being obtained from an external urine collection vessel. The collection vessel can be any of those collection vessels being disclosed herein. The electric, chemical or physical property of the urine being obtained can be processed by the frequency dependent component. In particular, frequency dependent component can be any such component disclosed herein e.g. the 555 circuit utilizing any of the methods described above. The external collection vessel have a sensor assembly comprising slave circuitry being controlled by the master processing unit; said device generates an output signal indicative of the urine measurement and records the output signal together with a time stamp being obtained from the real-time clock in the memory component.

The device can thus determine and accumulates a plurality of separate urine measurements and associates them with time stamps; thereby recording a 24 hour urination profile of a tested individual.

The dongle can be removably attachable to and from the disposable urine vessel, defining an attached configuration and a detached configuration and thereby facilitating electronic communication between the sensor and the external processing master unit.

Figure 7:
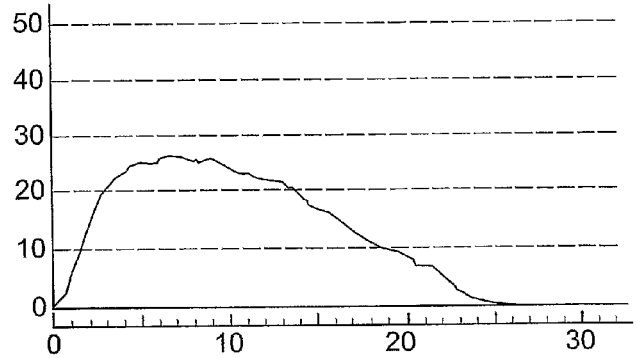
FIG. 7 shows a graph of urine flow measurements.
Figure 7:
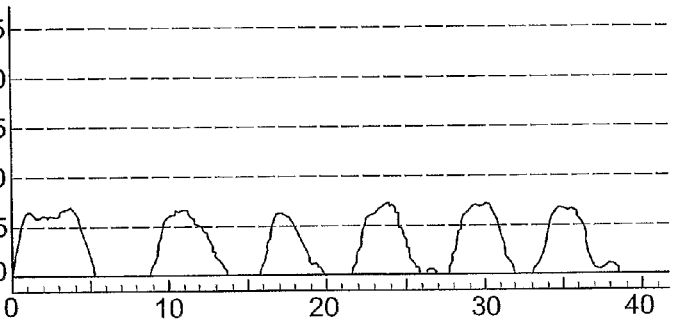
Figure 7:
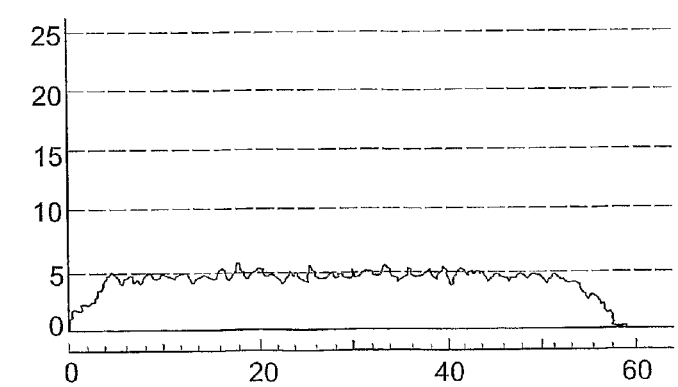

FIG. 7 shows a graph of urine flow measurement in 3 cases. Examples of normal urination Intermitted and Obstruction are provided. This information along with the quantitative data of urination (i.e. Qmax, Qavg) provides indicative diagnostic data for the physician. Where the handheld device for recording urine measurements configured and operates as urination diary, the indicative data information provided to the physician can also include a time stamp of every urine flow measurement or test performed. A time stamp is provided by a real time clock embedded in the device.

The invention claimed is:

1. A handheld integrated urine collection vessel, comprising:
a single use disposable receptacle comprising a side wall having interior and exterior side surfaces, a first conductive plate, a bottom plate and a single use disposable sensor assembly, the sensor assembly comprising at least one sensor and a slave circuitry; said sensor assembly is permanently affixed to said side surfaces or said bottom plate; said receptacle is configured to facilitate urine measurement insensitive to the horizontal angle of the receptacle;
wherein the receptacle is capable of maintaining the urine for a sufficient time period in the vicinity of the sensor thereby the sensor is operative to provide continuous measurement of an electric, chemical or physical property of the urine; said slave circuitry responds to electric, chemical or physical property of the urine received from the sensor and is configured and operable to electronically communicate the measurement of an electric, chemical or physical property of the urine to an external processing master unit;
wherein said sensor is a capacitive-sensor which is made of said first conductive plate which is disposed over said exterior side surface, said receptacle wall serving as a dielectric material, and the urine fluid serving as a second plate.

2. The handheld integrated urine collection vessel of claim 1 wherein the receptacle is configured to provide fluid contact between urine and the at least one sensor.

3. A handheld integrated urine collection vessel of claim 1 comprising a single use disposable urine funnel removably fitted in said receptacle; the urine funnel having a top opening to receive the collected urine from the user and is aligned with the receptacle to facilitate urine passage into the receptacle; the disposable urine funnel forces the collected urine to be disposed horizontally and uniformally on the inner surface of the bottom plate; thereby achieving uniform fluid contact of urine with collection vessel inner side surface.

4. The handheld integrated urine collection vessel of claim 3 wherein the master circuit feeds the slave circuitry of the receptacle with power supply.

5. The handheld integrated urine collection vessel of claim 1 wherein the sensor comprises a conductive plate.

6. The handheld integrated urine collection vessel of claim 1, comprising a receptacle interface adaptor, the external processing master unit is removably attachable to the receptacle interface adaptor thereby facilitating electronic communication between the sensor and the external processing master unit.

7. The handheld integrated urine collection vessel of claim 1, wherein the slave circuitry is configured and operable to continuously communicate plurality of said measurements to an external processing master unit; the master unit accumulates and determines the test results from said plurality of said measurement.

8. A handheld device a claim 7, wherein the device is removably attachable from the disposable urine receptacle, defining an attached configuration and a detached configuration and thereby facilitating electronic communication between the sensor and the external processing master unit.

9. A handheld device for recording urine measurements, wherein the device is configured and adapted to electronically communicate with the urine collection vessel of claim 1, the device comprises the processing master unit to receive and process the measurement of an electric, chemical or physical property of the urine being obtained from the sensor;
said device generates an output signal indicative of the urine measurement.

10. The handheld device of claims 9 comprising memory component for recording said urine measurements.

11. The device of claim 9 further comprising a real-time clock;
the device is configured to determine and accumulates a plurality of separate urine measurements and associates them with time stamps being obtained from the real-time clock;
thereby recording a 24-hour or more urine profile of a tested individual.

12. A handheld device of claim 9 wherein the handheld device is operable to have at least three states:
(i) an ONLINE state in which the handheld device is in operable communication with the sensor;
(ii) an OFFLINE state in which the handheld device is not in operable communication with the sensor; and
(iii) a SENSING state in which the handheld device in operable communication with the sensor and communicating measurement in real time.

13. The handheld device of claim 9 wherein said processor unit is configured and operable to receive and process measured data, in time, indicative of urine flow rate, urine volume, urine chemistry, urine biology.

14. The handheld device of claim 9 operative to exchange information relating to the urine measurement with a host controller of at least one of personal computer, remote computer or computer environment.

15. The handheld device of claim 9 connectible to an external memory utility for recording said urine measurements.

16. The handheld device of claim 15 wherein the memory utility is a removable Disk-on-Key memory device, USB stick, MMC, or SD.

17. A stationary device for recording urine measurements, the device is configured and adapted to electronically communicate with the handheld urine collection vessel of claim 1, the device comprises
the processing master unit to receive and process the measurement of an electric, chemical or physical property of the urine being obtained from the sensor;
said device generates an output signal indicative of the urine measurement;
said electronic communication being selected from wired or wireless communication;
the stationary device for recording urine measurements optionally includes a printer for printing an output indicative of said urine measurement.

18. A hardware dongle device for providing a 24hour urination diary, the dongle device capable of attaching and detaching from external sensors, comprises
a master processing unit, a frequency dependent component, memory component, an electric interface, real-time clock, and a communication port;
the device is configured and adapted to electronically communicate, receive, and process an external measurement of an electric, chemical or physical property of urine obtained from an external urine collection vessel, the processing being done by the frequency dependent component; the external collection vessel having a sensor assembly comprising slave circuitry being controlled by the master processing unit;
said device generates an output signal indicative of the urine measurement and records the output signal and a time stamp being obtained from the real-time clock in the memory component;
the device determine and accumulates a plurality of separate urine measurements and associates them with time stamps; thereby recording a 24hour urination profile of a tested individual.

19. A handheld integrated collection vessel of a bodily fluid, comprising:
a single use disposable receptacle for collection of a conductive bodily fluid comprising:
(a) inner and exterior side surfaces of a side wall said receptacle; and
(b) a bottom plate;
said side wall forms a dielectric substance;
a first conductive plate is permanently coupled to at least a portion of the exterior side surface so as to define a capacitive sensing volume within the receptacle;
wherein said collection vessel is configured and operable to continuously collect and maintain the conductive bodily fluid in fluid contact with said inner side surface during a fluid measurement procedure; during said fluid measurement procedure, the conductive bodily fluid forms a transient second plate-like opposing at least a surface area portion of said first conductive plate, thereby to form a capacitive sensor which is made of said first conductive plate, said receptacle wall serving as a dielectric material, and the conductive fluid serving as a second plate;
thereby facilitating an accurate electric, chemical or volumetric measurement procedure of the conductive bodily fluid.

* * * * *